US010676472B2

(12) United States Patent
Stanton et al.

(10) Patent No.: US 10,676,472 B2
(45) Date of Patent: Jun. 9, 2020

(54) CRYSTAL FORMS OF GLUTAMINASE INHIBITORS

(71) Applicant: Calithera Biosciences, Inc., South San Francisco, CA (US)

(72) Inventors: Timothy F. Stanton, Daly City, CA (US); James J. Springer, Saugatuck, MI (US); Jacqueline N. Williams, West Lafayette, IN (US)

(73) Assignee: Calithera Biosciences, Inc., South San Francisco, CA (US)

( * ) Notice: Subject to any disclaimer, the term of this patent is extended or adjusted under 35 U.S.C. 154(b) by 0 days.

(21) Appl. No.: 16/434,872

(22) Filed: Jun. 7, 2019

(65) Prior Publication Data

US 2019/0359607 A1  Nov. 28, 2019

Related U.S. Application Data

(63) Continuation of application No. 15/501,622, filed as application No. PCT/US2015/044301 on Aug. 7, 2015, now Pat. No. 10,316,030.

(60) Provisional application No. 62/034,547, filed on Aug. 7, 2014.

(51) Int. Cl.
| | | |
|---|---|---|
| *C07D 417/14* | (2006.01) | |
| *A61K 31/501* | (2006.01) | |
| *A61K 45/06* | (2006.01) | |

(52) U.S. Cl.
CPC .......... *C07D 417/14* (2013.01); *A61K 31/501* (2013.01); *A61K 45/06* (2013.01); *C07B 2200/13* (2013.01)

(58) Field of Classification Search
CPC ................................................. C07D 285/135
See application file for complete search history.

(56) References Cited

U.S. PATENT DOCUMENTS

| | | | |
|---|---|---|---|
| 6,451,828 | B1 | 9/2002 | Newcomb et al. |
| 8,604,016 | B2 | 12/2013 | Li et al. |
| 8,865,718 | B2 | 10/2014 | Li et al. |
| 9,687,485 | B2 | 6/2017 | Steggerda et al. |
| 9,938,267 | B2 | 4/2018 | Li et al. |
| 1,019,519 | A1 | 2/2019 | Bennett et al. |
| 10,258,619 | B2 | 4/2019 | Molineaux et al. |
| 10,278,968 | B2 | 5/2019 | Parlati et al. |
| 10,316,030 | B2 | 6/2019 | Stanton et al. |
| 10,441,587 | B2 | 10/2019 | Parlati et al. |
| 2002/0115698 | A1 | 8/2002 | Newcomb et al. |
| 2004/0198716 | A1 | 10/2004 | Arad et al. |
| 2005/0260697 | A1 | 11/2005 | Wang et al. |
| 2010/0330197 | A1 | 12/2010 | Higashiguchi et al. |
| 2012/0302605 | A1 | 11/2012 | DeWitt |
| 2013/0109643 | A1 | 5/2013 | Riggins et al. |
| 2013/0157998 | A1* | 6/2013 | Li ..................... C07D 285/135 514/210.18 |
| 2014/0050699 | A1 | 2/2014 | Li et al. |
| 2014/0142081 | A1 | 5/2014 | Lemieux et al. |
| 2014/0142146 | A1 | 5/2014 | Lemieux et al. |
| 2014/0194421 | A1 | 7/2014 | Li et al. |
| 2014/0369961 | A1 | 12/2014 | Li et al. |
| 2015/0004134 | A1 | 1/2015 | Bennett et al. |
| 2015/0258082 | A1 | 9/2015 | Parlati et al. |
| 2016/0010158 | A1 | 1/2016 | Wang et al. |
| 2016/0022674 | A1 | 1/2016 | Steggerda et al. |
| 2016/0287564 | A1 | 10/2016 | Gross et al. |
| 2016/0287585 | A1 | 10/2016 | Parlati et al. |
| 2017/0095473 | A1 | 4/2017 | Molineaux et al. |
| 2017/0226101 | A1 | 8/2017 | Stanton et al. |
| 2017/0333430 | A1 | 11/2017 | Steggerda et al. |
| 2017/0369485 | A1 | 12/2017 | Li et al. |
| 2018/0055825 | A1 | 3/2018 | Liang et al. |
| 2018/0055842 | A1 | 3/2018 | Bennett et al. |
| 2018/0055843 | A1 | 3/2018 | Parlati et al. |

FOREIGN PATENT DOCUMENTS

| | | |
|---|---|---|
| JP | 2012/165736 A | 9/2012 |
| WO | WO-2009/017822 A2 | 2/2009 |
| WO | WO-2011/143160 A2 | 11/2011 |
| WO | WO-2012/006506 A1 | 1/2012 |
| WO | WO-2013/034806 A1 | 3/2013 |
| WO | WO-2013/044596 A1 | 4/2013 |
| WO | WO-2013/078123 A1 | 5/2013 |
| WO | WO-2013/177426 A2 | 11/2013 |
| WO | WO-2014/039960 A1 | 3/2014 |
| WO | WO-2014043633 A1 | 3/2014 |
| WO | WO-2014/078645 A1 | 5/2014 |
| WO | WO-2014/079136 A1 | 5/2014 |
| WO | WO-2014/079150 A1 | 5/2014 |
| WO | WO-2014/081925 A1 | 5/2014 |

(Continued)

OTHER PUBLICATIONS

Altman et al., "From Krebs to Clinic: Glutamine Metabolism to Cancer Therapy," Nat Rev Cancer, 6(10):619-634 (2016).
Asahara et al., Yozaihandobukku (solvent handbook), Kodansha Ltd., 47-51 (1985).
Berge et al., "Pharmaceutical Salts," Journal of Pharmaceutical Sciences, 66(1):1-19 (1977).
Borodovsky et al., "5-azacytidine reduces methylation, promotes differentiation and induces tumor regression in a patient-derived IDH1 mutant glioma xenograft," Oncotarget, 4(10): 1737-1737 (Sep. 16, 2013).
Bromley-Dulfano, et al., "Antitumor activity of the glutaminase inhibitor CB-839 in hematological malignances," Blood, 122(21): 4226 (2013).
CAS Registry No. 714283-67-7 STN Entry Date Jul. 22, 2004.
CAS RN 1400068-83-8 STN Entry Date Oct. 8, 2012; N,N1-(5,51-(pentane-1,5-diyl)]bis(1,3,4-thiadiazole-5,2-diyl))bis(2-methoxybenzamide).
CAS RN 331234-76-5, STN Entry Date Apr. 13, 2001; N,N1-[thiobis(2,1-ethanediyl-1,3,4-thiadiazole-5,2-diyl)]bis-1H-1,2,4-triazole-3-carboxmide.

(Continued)

*Primary Examiner* — Paul V Ward
(74) *Attorney, Agent, or Firm* — Foley Hoag LLP

(57) ABSTRACT

The invention relates to crystalline salts of a compound having the structure of formula (I), methods for their preparation, and related pharmaceutical compositions comprising the crystalline salt. The invention further relates to methods of treating or preventing cancer or an immunological or neurological disease comprising administering a crystalline salt of the invention.

16 Claims, 7 Drawing Sheets

(56) References Cited

FOREIGN PATENT DOCUMENTS

Figure 1:
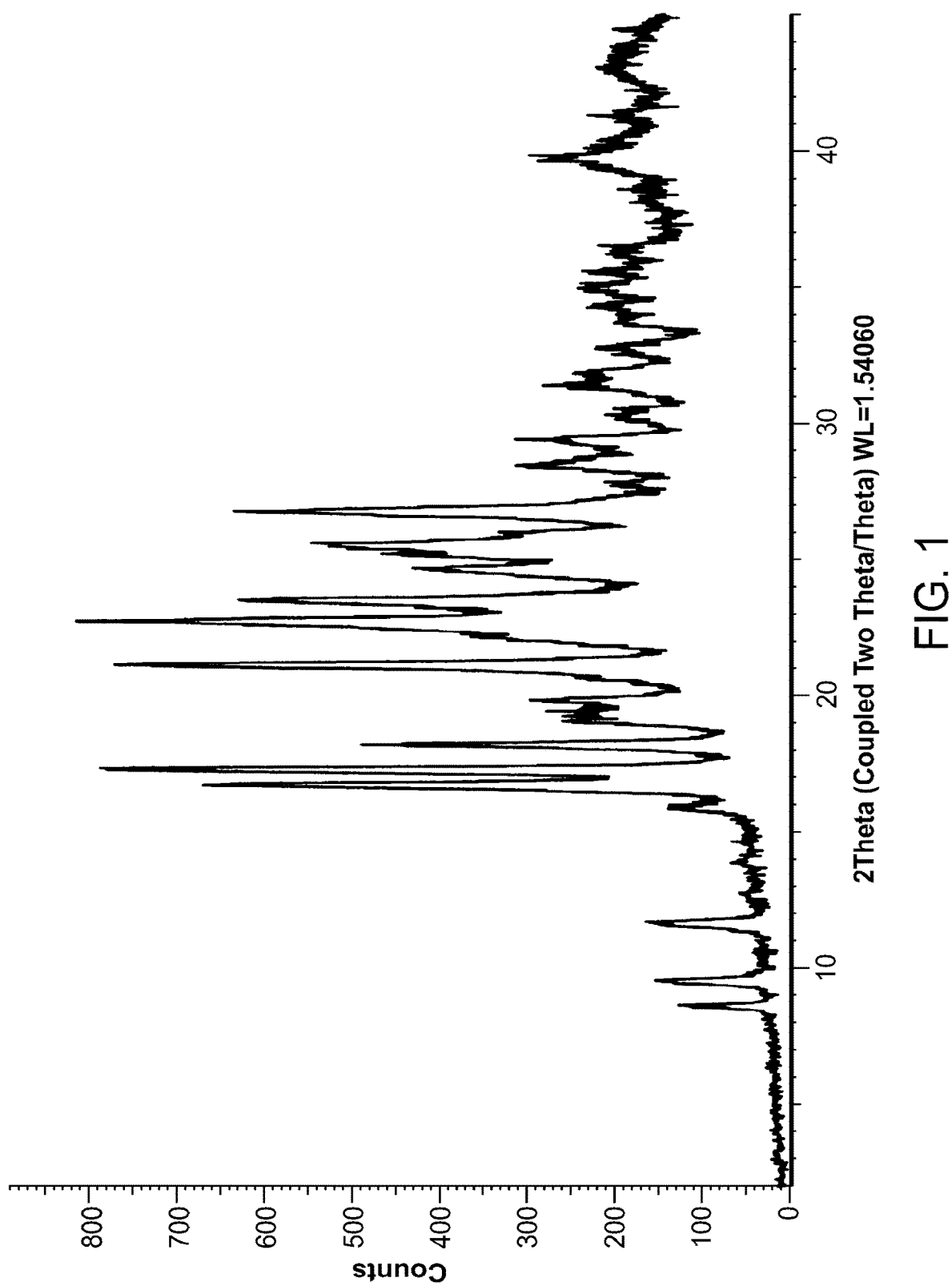

| | | | |
|---|---|---|---|
| WO | WO-2014/089048 A1 | 6/2014 |
| WO | WO-2015/061432 A1 | 4/2015 |
| WO | WO-2015/138902 A1 | 9/2015 |
| WO | WO-2015/192014 A1 | 12/2015 |
| WO | WO-2016/004418 A1 | 1/2016 |
| WO | WO-2016/014890 A1 | 1/2016 |
| WO | WO-2016/022969 A1 | 2/2016 |
| WO | WO-2016/054388 A1 | 4/2016 |
| WO | WO-2016/077632 A2 | 5/2016 |
| WO | WO-2016/160980 A1 | 10/2016 |
| WO | WO-2016/164401 A1 | 10/2016 |
| WO | WO-2017/062354 A1 | 4/2017 |
| WO | WO-2018/039441 A1 | 3/2018 |
| WO | WO-2018/039442 A1 | 3/2018 |
| WO | WO-2018/039544 A1 | 3/2018 |
| WO | WO-2018/165516 A1 | 9/2018 |

OTHER PUBLICATIONS

Chemical Abstract Registry No. 296888-91-0, indexed in the Registry File on STN CAS Online Oct. 18, 2000.
Chemical Abstract Registry No. 666208-63-5, indexed in the Registry File on STN CAS Online Mar. 22, 2004.
Chen et al., "Targeting glutamine induces apoptosis: a cancer therapy approach," Int J Mol Sci, 16(9):22830-22855 (2015).
Clinical Trials, "Study of the Glutaminase Inhibitor CB-839 in Solid Tumors," ClinicalTrials.gov (2016).
Costello et al., "Evidence for changes in RREB-1, ZIP3, and zinc in the early development of pancreatic adenocarcinoma," J Gastrointest Cancer, 43:570-8 (2012).
Dai et al., "Studies on the novel a-glucosidase inhibitory activity and structure-activity relationships for andrographolide analogues," Bioorg Med Chem Lett, 16:2710-13 (2006).
DeLabarre B.et al., "Full-Length Human Glutaminase in Complex with an Allosteric Inhibitor", Biochem, 50:1-27 (2011).
Extended European Search Report issued by the European Patent Office in corresponding Application No. 15830024.4, dated Nov. 24, 2017.
Filipp et al., "Glutamine-fueled mitochondrial metabolism is decoupled from glycolysis in melanoma," Pigment Cell Melanoma Res, 25:732-739 (2012).
Fujiwara et al., "First-principles and direct design approaches for the control of pharmaceutical crystallization," Journal of Process Control, 15(5):493-504 (2005).
Gameiro et al., "In Vivo HIF-Mediated Reductive Carboxylation is Regulated by Citrate Levels and Sensitizes VHL-Deficient Cells to Glutamine Deprivation," Cell Metabolism, 17:372 (2013).
Gao et al., "c-Myc suppression of miR-23a/b enhances mitochondrial glutaminase expression and glutamine metabolism," Nature, 458(7239):762-5 (2009).
Gehlen H. et al., "Uber die Einwirkung von Isocyanaten auf substituierte 2-Amino-1,3,4-oxdiazole", Justus Leibigs Annalen der Chemie, vol. 692, pp. 151-165 (1966).
Gehlen, H., et al. "Uber die Acylierung der 2-Amino-5-(alkyl, aryl)-1.3.4-oxidazole," Leibeigs Ann. Chem. 703: 131-135 (1967).
Gennaro, A., Remington's Pharmaceutical Sciences. Easton, PA:Mack Pub. Co., 1990.
Gross et al., "Antitumor Activity of the Glutaminase Inhibitor CB-839 in Triple-Negative Breast Cancer", Mol. Cancer Ther., 13(4):890-901 (2014).
Haynes et al., "Occurrence of Pharmaceutically Acceptable Anions and Cations in the Cambridge Structural Database," J Pharm Sci, 94: 2111-2120 (2005).
Hensley et al., "Glutamine and cancer: Cell biology, physiology, and clinical opportunities," J Clin Investig, 123(9):3678-84 (2013).
Holliday et al., "Choosing the right cell line for breast cancer research," Breast Cancer Res, 13:215 (2011).
Horig et al., "From bench to clinic and back: Perspective on the 1st IQPC Translational Research conference", *Journal of Translational Medicine*, vol. 2, p. 44 (2004).

International Search Report and Written Opinion for PCT/US2015/035577 dated Sep. 20, 2015.
International Search Report for Application No. PCT/US2016/026127, dated Jul. 27, 2016.
International Search Report for PCT/US2012/065816 dated Feb. 1, 2013.
International Search Report from International Application No. PCT/US2013/070277 dated Feb. 13, 2014.
International Search Report from International Application No. PCT/US2013/072830 dated Mar. 4, 2014.
Ito et al., "A medium-term rat liver bioassay for rapid in vivo detection of carcinogenic potential of chemicals," Cancer Science, 94(1):3-8 (2003).
Jacque, et al., "Targeting glutaminolysis has antileukemic activity in acute myeloid leukemia and synergizes with BCL-2 inhibition," Blood, 126(11): 1346-1356 (2015).
Janne et al., "Factors underlying sensitivity of cancers to small-molecule kinase inhibitors," Nat Rev Drug Discov, 8:709-723 (2009).
Johnson et al., "Relationships between drug activity and NCI preclinical in vitro and in vivo models and early clinical trials," Brit J Cancer, 84(10):1424-31 (2001).
Kim, A., "Clinical impact of gene expression profiling on oncology diagnosis, prognosis, and treatment," Combinatorial Chem & High Throughput Screening, 7:183-206 (2004).
Kung et al., "Glutamine synthetase is a genetic determinant of cell type-specific glutamine independence in breast epithelia," PLOS Genetics, 7(8):e1002229 (2011).
Lee, "A practical guide to pharmaceutical polymorph screening & selection," Asian Journal of Pharmaceutical Sciences, 9(4):163-175 (2014).
Martin et al., "Do structurally similar molecules have similar biological activity?" J Med Chem, 45:4350-8 (2002).
McCleland, et al., "Lactate dehydrogenase B is required for the growth of KRAS-Dependent lung adenocarcinomas," Clin Cancer Res, 19(4): 773-784 (2013).
Medina, M., "Glutamine and cancer," J Nutr, 131(9 Suppl):2539S-42S (2001).
Nars et al., "Immunomodulatory effects of low dose chemotherapy and perspectives of its combination with immunotherapy," Int J Cancer, 132(11):2471-2478 (2013).
Newman et al., "Chapter 1: from selection of pharmaceutical compounds," Handbook of Pharmaceutical Analysis, New York: Marcel Dekker, (2002).
Osol, A. [Editor]. "Chapter 27: Structure-activity relationship and drug design," Remington's Pharmaceutical Sciences (Sixteenth Edition). 1980. pp. 420-435.
Pajic et al., "Cell cycle activation by c-myc in a Burkitt's lymphoma model cell line", *International Journal of Cancer*, vol. 87, pp. 787-793 (2000).
Parlati et al., "Antitumor Activity of the Glutaminase Inhibitor CB-839 in Hematological Malignances", 55th ASH Annual Meeting and Exposition, Dec. 9, 2013, New Orleans, LA, abstract No. 4226.
Parlati et al., "Glutaminase inhibitor CB-839 synergizes with pomalidomide in preclinical multiple myeloma models," American Society of Hematology Annual Meeting—Dec. 6-9, 2014.
Prat et al., "Phenotypic and molecular characterization of the claudin-low intrinsic subtype of breast cancer," Breast Cancer Res, 12(5):R68 (2010).
Rajagopalan K.N. et al., "Role of Glutamine in Cancer: Therapeutic and Imaging Implications", *Journal of Nuclear Medicine*, vol. 52, pp. 1005-1008 (2011).
Robinson et al., "Novel mechanism of inhibition of rat kidney-type glutaminase by bis-2-(5-phenylacetamido-1,2,4-thiadiazol-2-yl)ethyl sulfide (BPTES)," Biochem. J., 406:407-414 (2007).
Schäfer et al., "Failure is an option: learning from unsuccessful proof-of-concept trials", *Drug Discovery Today*, vol. 13, pp. 913-916 (2008).
Seltzer et al., "Inhibition of glutaminase preferentially slows growth of glioma cells with mutant IDH1", *Cancer Research*, vol. 70, pp. 8981-8987 (2010).
Sharma et al., "Anti-myeloma activity of a novel glutaminase inhibitor CB-839," Blood, vol. 124(21): 4226 (2014).

(56) References Cited

OTHER PUBLICATIONS

Shimano Y. et al., "Synthesis of Poly(diacylthiosemicarbazide)s from Diacylisothiocyanates and Dihydrazides, and Their Thermal Cyclodehydration" Kobunshi Ronbunshu, vol. 37, No. 2, pp. 131-137 (1980).
Shukla, K., et al, "Design, Synthesis and Pharmacological Evaluation of Bis-2-(5-phenylacetamido-1-2, 4-thiadiazol-2-yl)ethyl 1 sulfide 3 (BPTES) Analogs as Glutaminase Inhibitors", *Journal of Medicinal Chemistry*, vol. 55, No. 23, pp. 10551-10563 (2012).
Simpson et al., "Modifying metabolically sensitive histone marks by inhibiting glutamine metabolism affects gene expression and alters cancer cell phenotype," Epigenetics, 7(12):1413-20 (2012).
Son et al., "Glutamine supports pancreatic cancer growth through a KRAS-regulated metabolic pathway," Nature, 496:101-105 (2013).
Sporn et al., "Chemoprevention of cancer," Carcinogenesis, 21(3):525-30 (2000).
Stahl et al., "Chapter 8.1.9. Other Organic Acids," Handbook of Pharmaceutical Salts: Properties, Selection, and use, 214 (2002).
Thangavelu, K. et al., "Structural basis for the allosteric inhibitory mechanism of human kidney-type glutaminase (KGA) and its regulation by Raf-Mek-Erk signaling in cancer cell metabolism", *Proceedings of the National Academy of Sciences of the United States of America*, vol. 109, No. 20, pp. 7705-7710 (2012).
The 4th Edition, Experimental Chemistry 1, Kihonsousa I (basic operations I), Maruzen Publishing Co., 184-189 (1996).
Thoppil et al., "Terpenoids as potential chemopreventive and therapeutic agents in liver cancer," World J Hepatol, 3(9):228-249 (2011).
Tseng, et al., "The synthesis of daidzein derivatives," J Natural Taiwan Normal University, 30:537-545 (1985).
Vaishampayan, "Cabozantinib as a Novel Therapy for Renal Cell Carcinoma," Curr. Oncol. Rep. 15:76-82 (2013).
van den Heuvel et al., "Analysis of glutamine dependency in non-small cell lung cancer: GLS1 splice variant GAC is essential for cancer cell growth," Cancer Biol Ther, 13(12):1185-94 (2012).
Variankaval et al., "From form to function: crystallization of active pharmaceutical ingredients," AIChE Journal, 54(7):1682-1688 (2008).
Voskoglou-Nomikos et al., "Clinical predictive value of the in vitro cell line, human xenograft, and mouse allograft preclinical cancer models," Clin Cancer Res, 9:4227-39 (2003).
Wang et al., "Targeting mitochondrial glutaminase activity inhibits oncogenic transformation," Cancer Cell, 18(3):207-19 (2010).
Written Opinion of the International Searching Authority for Application No. PCT/US2016/026127, dated Jul. 27, 2016.
Xiang et al., "Targeted inhibition of tumor-specific glutaminase diminishes cell-autonomous tumorigenesis," J Clin Invest, 125(6):2293-2306 (2015).
Zhao et al., "Targeting Cellular Metabolism to Improve Cancer Therapeutics," Cell Death & Disease 4(3):e532 (2013).
Zimmerman, et al., "Allosteric glutaminase inhibitors based on a 1,4-Di(5-amino-1,3,4-thiadiazol-2-yl)butane scaffold," ACS Med Chem Lett, 7(5): 520-524 (2016).
Braga et al, "Crystal polymorphism and multiple crystal forms," Struct Bond 132:25-50 (2009).
Extended European Search Report for EP application No. EP 19189654 dated Nov. 18, 2019.
Guidance for Industry "Food-Effect Bioavailability and Fed Bioequivalence Studies," Food and Drug Administration, Center for Drug Evaluation and Research 12 (2002).
Hilfiker et al, "Relevance of Solid-State Properties for Pharmaceutical Products" Polymorphism: in the Pharmaceutical Industry 1:1-19 (2006).
Nankervis et al., "Thiophene inhibitors of PDE4: Crystal structures show a second binding mode at the catalytic domain of PDE4D2," Bioorg Med Chem Letts 21(23):7089-7093 (2011).
NCT02071862 (ClinicalTrials.gov, Feb. 24, 2014, 5 pages) (Accessed from https://www.clinicaltrials.gov/ct2/history/NCT02071862 on Aug. 12, 2019) (2014).
NCT02071927 (ClinicalTrials.gov, Feb. 24, 2014, 5 pages) (Accessed from https://clinicaltrials.gov/ct2/history/NCT02071927 on Aug. 12, 2019) (2014).
Peterson et al., "Expanding the Scope of Crystal Form Evaluation in Pharmaceutical Science." J Pharm Pharmaceut Sci, 9(3):317-326 (2006).
Winstanley et al., "The effects of food on drug bioavailability," Br J Clin Pharmac 28:621-628 (1989).

\* cited by examiner

CRYSTAL FORMS OF GLUTAMINASE INHIBITORS

RELATED APPLICATIONS

This application claims the benefit of priority to U.S. Provisional Patent Application Ser. No. 62/034,547, filed Aug. 7, 2014, the contents of which are hereby incorporated by reference.

BACKGROUND

Glutamine supports cell survival, growth and proliferation of cancer cells through metabolic and non-metabolic mechanisms. In actively proliferating cells, the metabolism of glutamine is a major source of building blocks and energy for the cells. When glutamine is withdrawn from the media in which the cancer cells are grown, the cells frequently stop growing or die. In cancer cells, much of the glutamine that is taken up by the cells is converted to glutamate through the action of the enzyme glutaminase. Thus, conversion of glutamine to glutamate via glutaminase is a control point for glutamine metabolism.

Ever since Warburg's observation that ascites tumor cells exhibited high rates of glucose consumption and lactate secretion in the presence of oxygen, researchers have been exploring how cancer cells utilize metabolic pathways to be able to continue actively proliferating. Several reports have demonstrated how glutamine metabolism supports macromolecular synthesis necessary for cells to replicate.

Thus, glutaminase has been theorized to be a potential therapeutic target for the treatment of diseases characterized by actively proliferating cells, such as cancer. The lack of suitable glutaminase inhibitors with good pharmaceutical properties has made it difficult to develop glutaminase inhibitors for clinical use. Therefore, the creation of glutaminase inhibitors that are specific and capable of being formulated for in vivo use could lead to a new class of therapeutics. Specifically, what is needed are improved compositions and methods for preparing and formulating glutaminase inhibitors.

SUMMARY OF INVENTION

One aspect of the invention relates to a crystalline compound or a crystalline salt of a compound having the structure of formula (I),

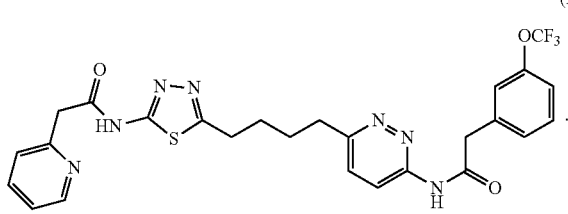

(I)

Another aspect of the invention relates to methods for preparing the crystalline compounds and crystalline salts of formula (I).

In certain embodiments, the present invention provides a pharmaceutical preparation suitable for use in a human patient, comprising a crystalline compound or a crystalline salt of a compound of formula (I), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient.

The present invention further provides methods of treating or preventing cancer, immunological or neurological diseases as described herein, comprising administering a crystalline compound or a crystalline salt of the invention.

DETAILED DESCRIPTION OF THE DRAWINGS

Figure 2:
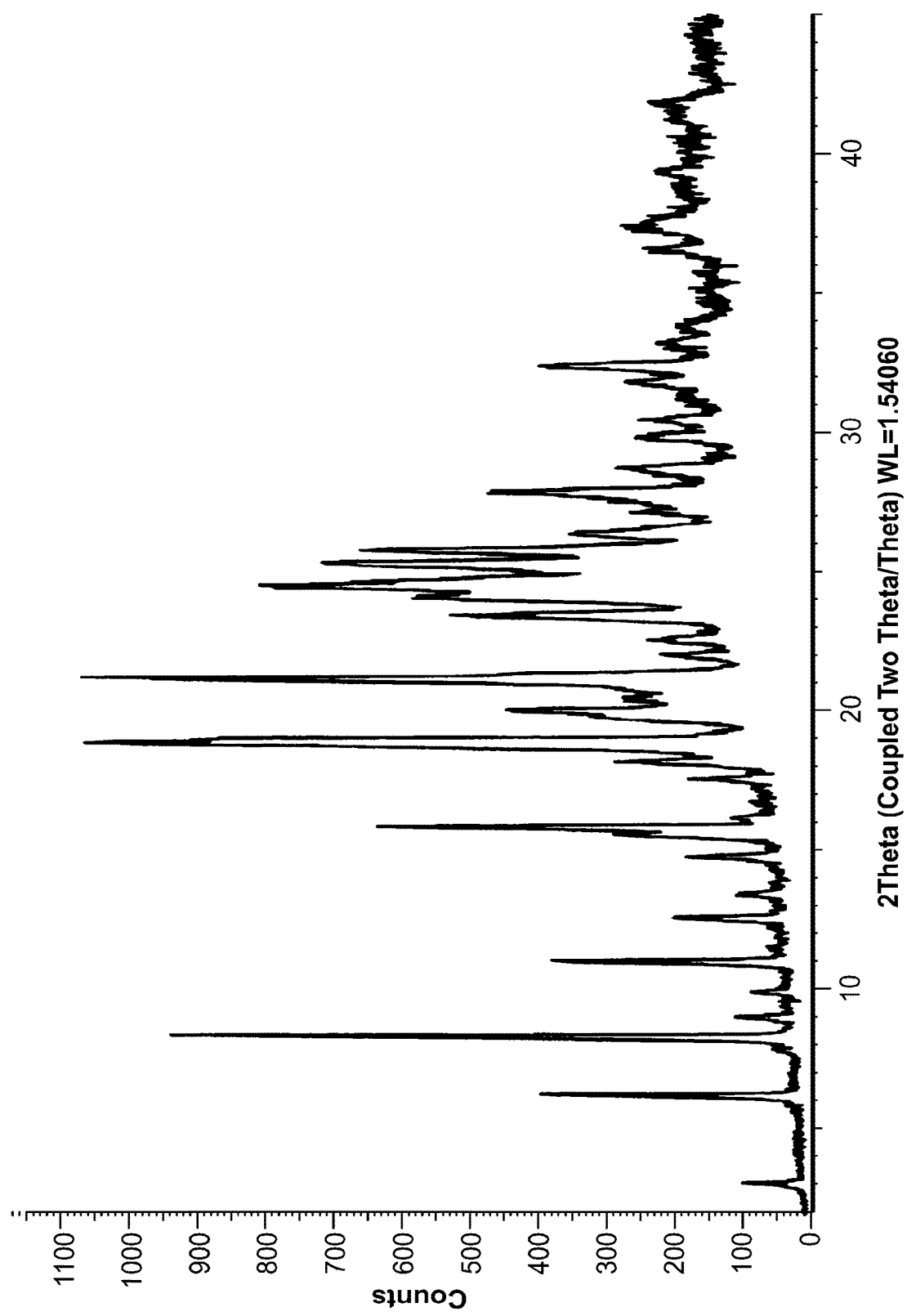
Figure 3:
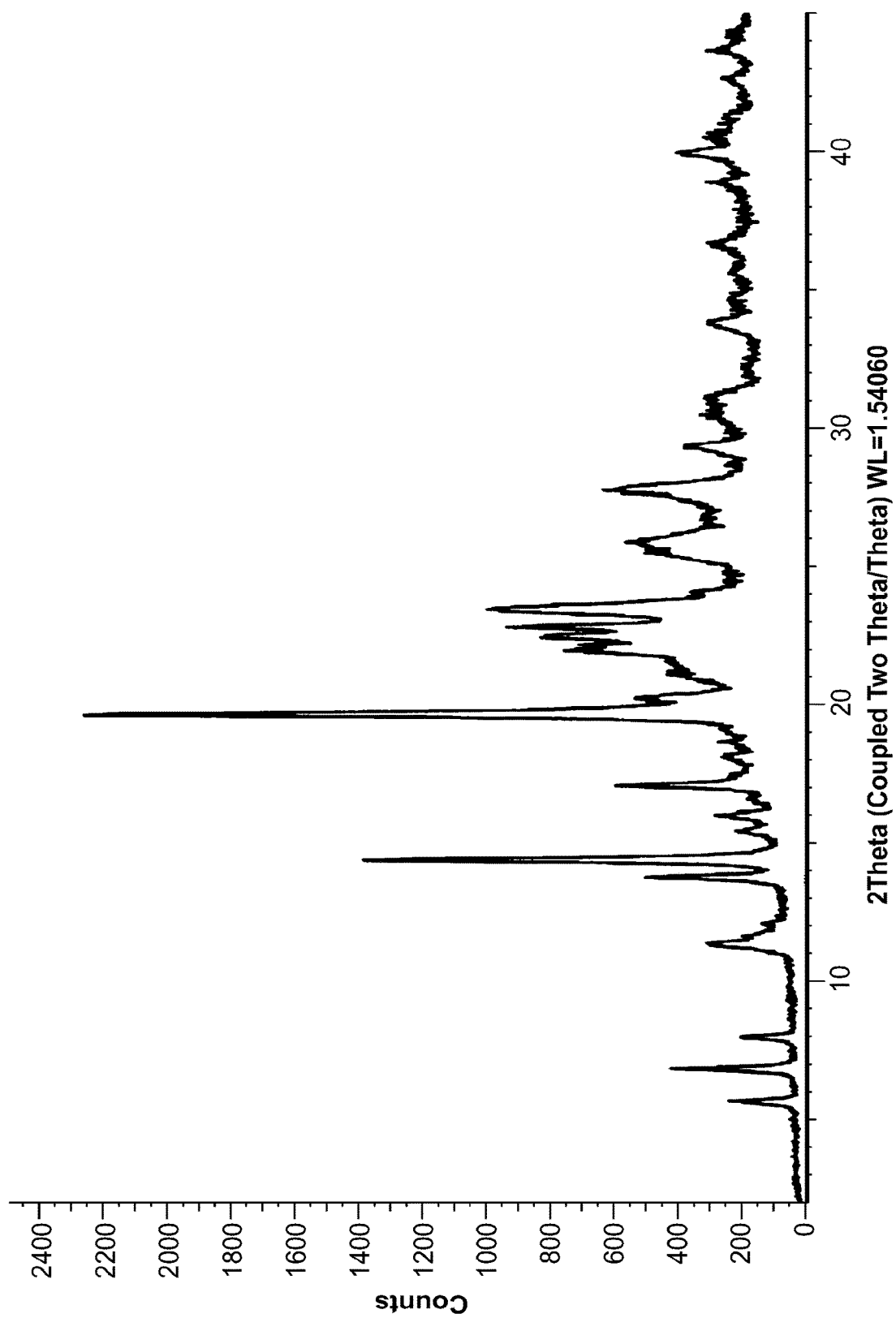
Figure 4:
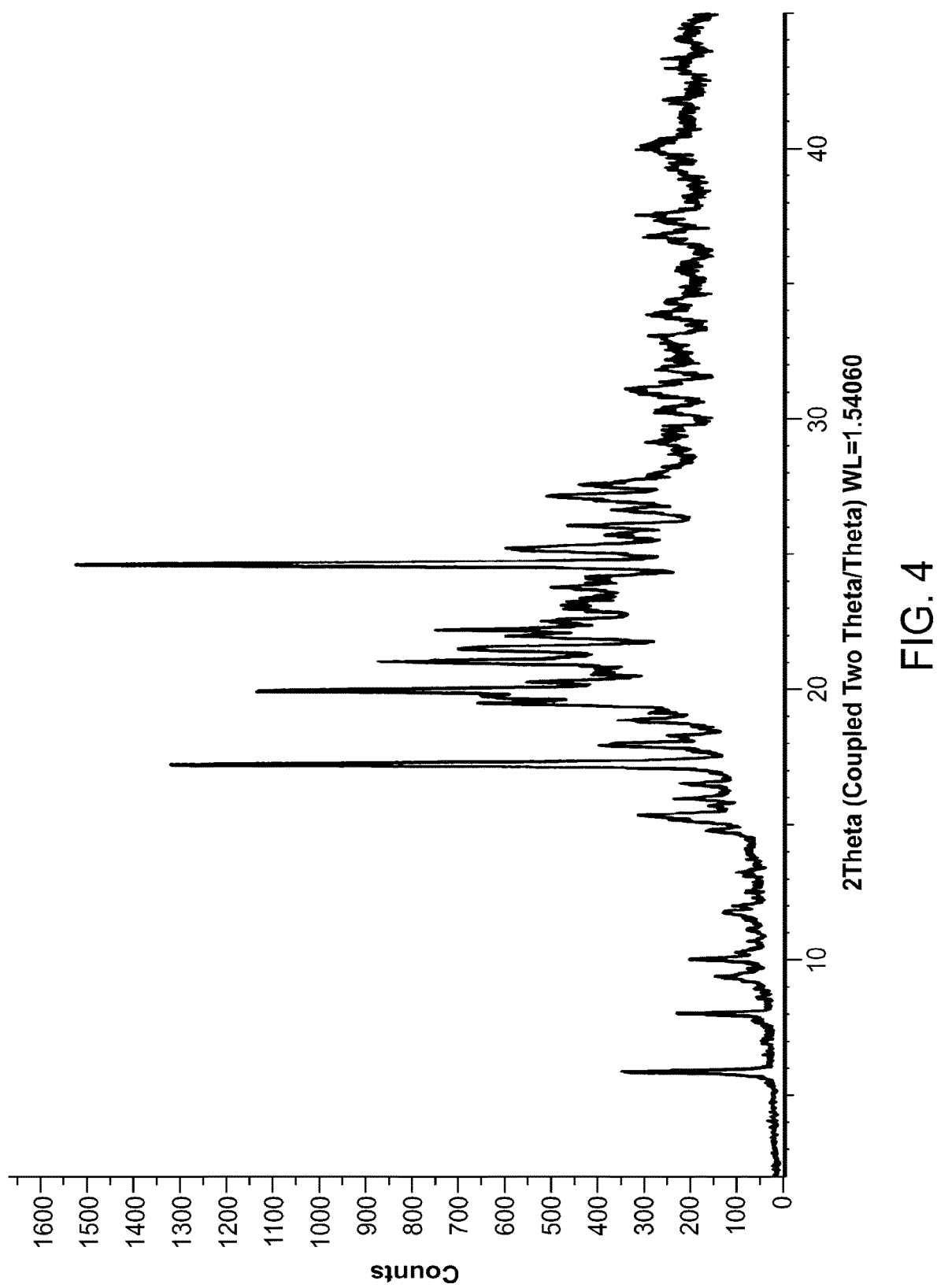
Figure 5:
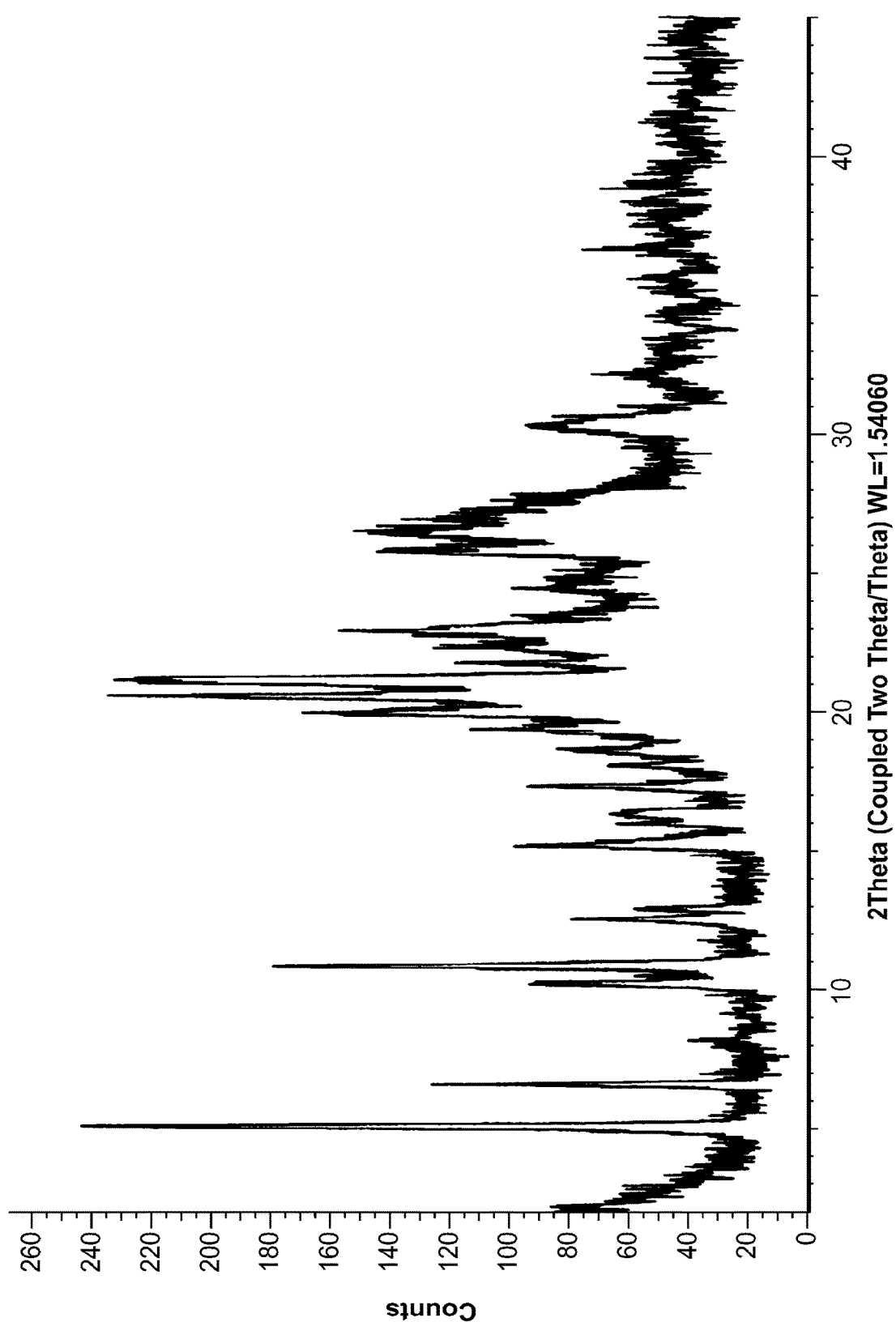
Figure 6:
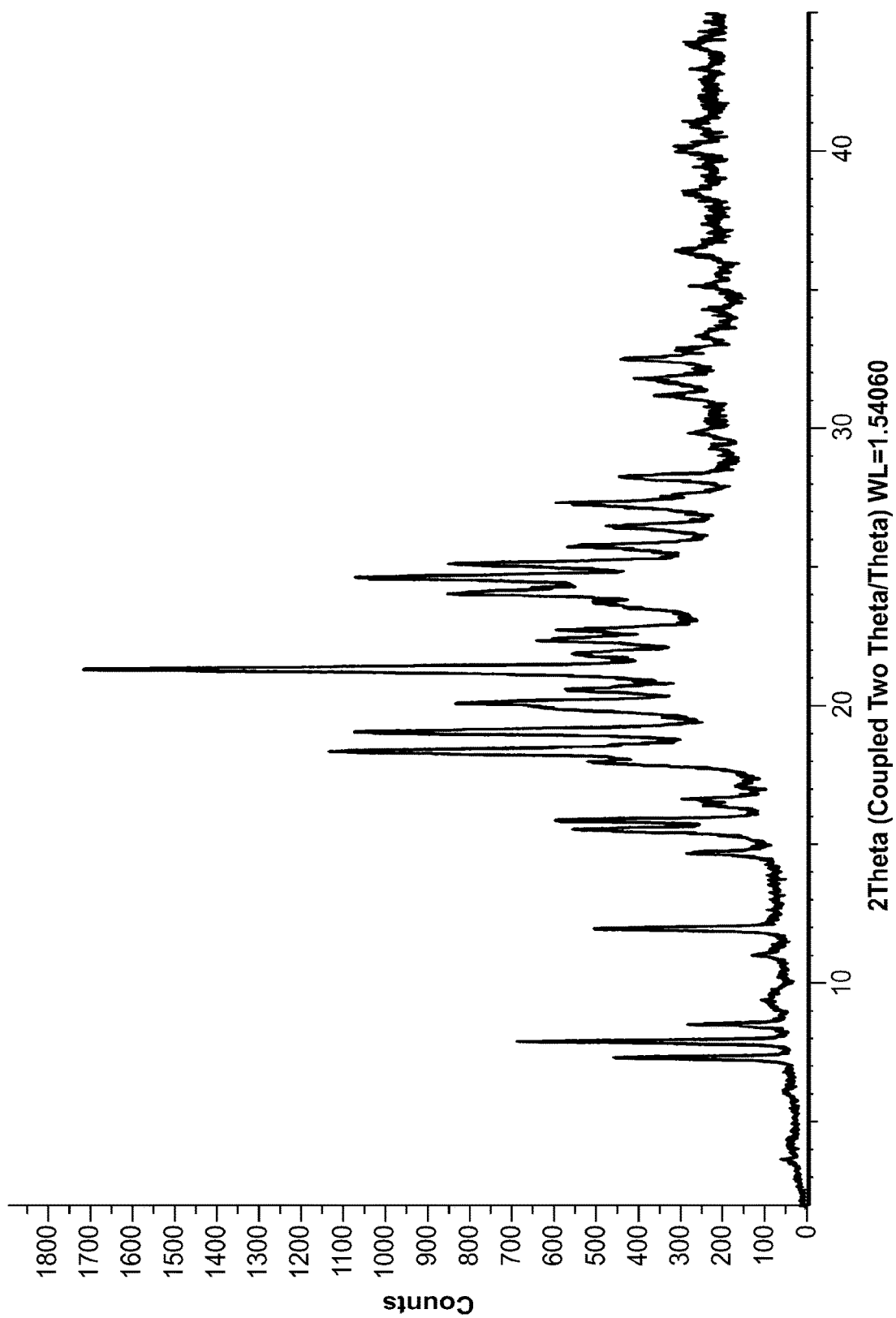
Figure 7:
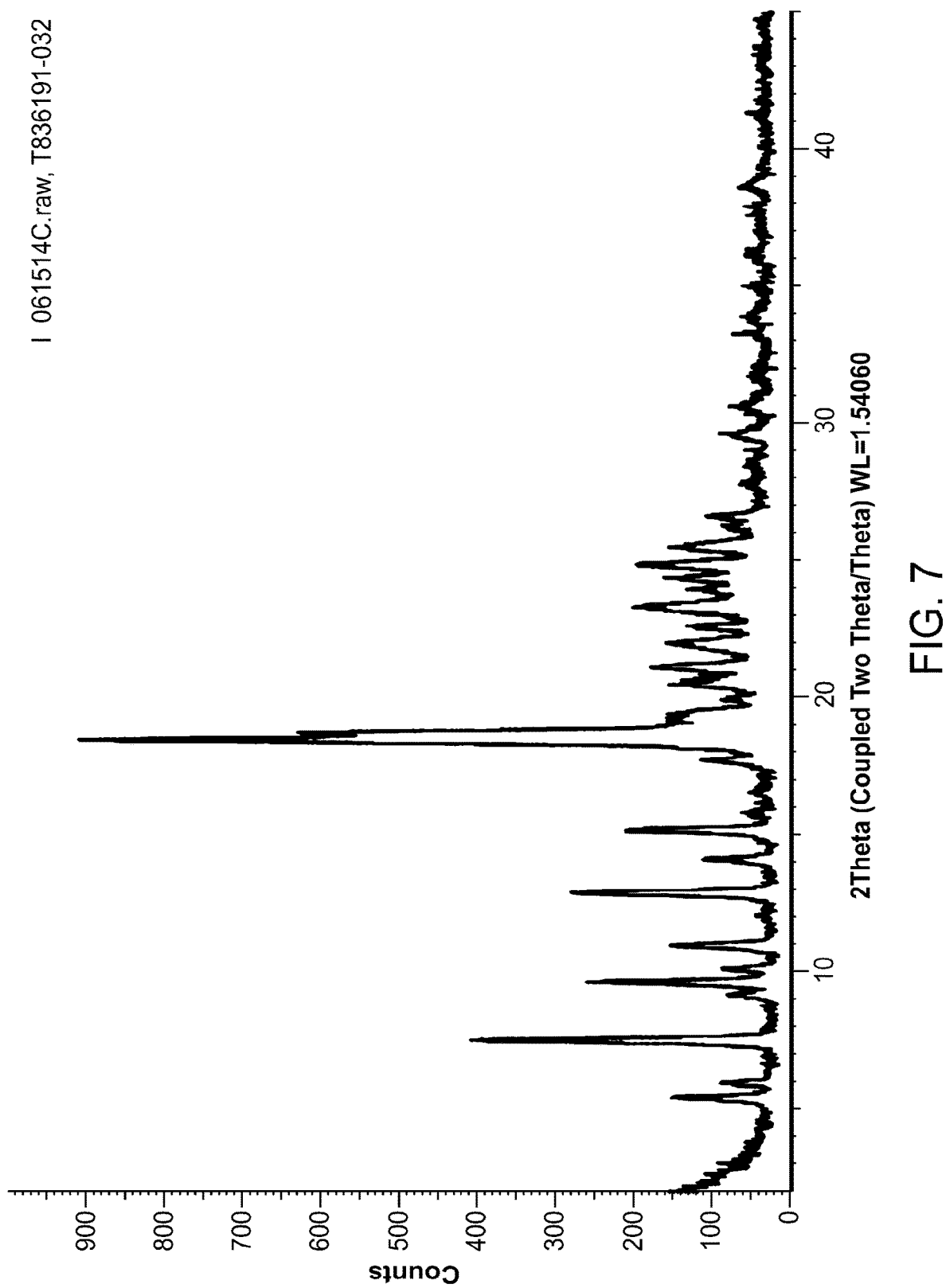

FIG. 1 is a X-ray diffraction (XRD) pattern of CB-839 HCl, Form I.
FIG. 2 is an XRD pattern of CB-839 HCl, Form II.
FIG. 3 is an XRD pattern of CB-839 TsOH.
FIG. 4 is an XRD pattern of CB-839 MsOH.
FIG. 5 is an XRD pattern of CB-839 HBr.
FIG. 6 is an XRD pattern of CB-839, free base, Form B.
FIG. 7 is a XRD pattern of CB-839, free base, Form A.

DETAILED DESCRIPTION OF THE INVENTION

In certain embodiments, the invention provides a crystalline compound having the structure of formula (I), or a crystalline salt of a compound having the structure of formula (I),

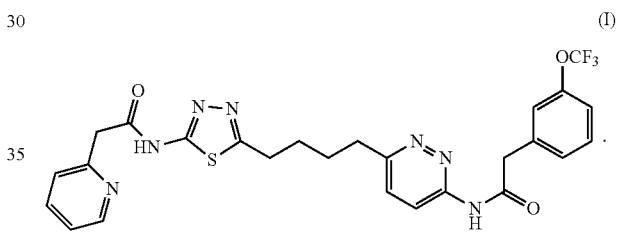

(I)

In certain embodiments, the present invention provides a pharmaceutical preparation comprising a crystalline compound or a crystalline salt of a compound of formula (I) and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient.

In certain embodiments, the present invention relates to methods of treating or preventing cancer or an immunological or neurological disease comprising administering a crystalline compound or a crystalline salt of a compound of formula (I).

In certain embodiments, the invention relates to a method for preparing a crystalline salt of a compound having the structure of formula (I), comprising a) providing a freebase slurry of a compound of formula (I) in a first organic solvent; b) contacting the freebase slurry with a reagent solution comprising an acid and optionally a second organic solvent under conditions sufficient to form a mixture comprising a salt of the compound of formula (I); and c) crystallizing the salt of the compound of formula (I) from the mixture comprising a salt of the compound of formula (I).

Any crystalline compound or a crystalline salt thereof described herein may be used in the manufacture of a medicament for the treatment of any diseases or conditions disclosed herein.

In certain embodiments, the crystalline salt is a hydrochloride salt, a toluenesulfonate salt, a nitrate salt, a methanesulfonate salt, or a hydrobromide salt. In particular embodiments, the crystalline salt is a hydrochloride salt.

In certain embodiments, the salts of the present invention can assemble into more than one crystal formation. In an exemplary embodiment, the crystalline hydrochloride salt of the compound having the structure of formula (I) exists as "form I" and "form II", as described in detail below.

In certain embodiments, the polymorph of the crystalline salt is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, form I of the crystalline HCl salt has 2θ values 16.70; 17.26; 21.09; and 22.69. In further embodiments, form I has 2θ values 16.70; 17.26; 18.18; 21.09; 22.69; 23.46; 25.22; 25.49; and 26.72. In yet further embodiments, form I has 2θ values 9.53; 11.63; 16.70; 17.26; 18.18; 19.10; 19.80; 21.09; 22.16; 22.69; 23.46; 24.63; 25.22; 25.49; 25.91; 26.72; 28.45; 29.38; 31.39; 31.82; and 34.91. In yet further embodiments, form I has 2θ values 8.62; 9.53; 11.63; 15.89; 16.70; 17.26; 18.18; 19.10; 19.80; 21.09; 22.16; 22.69; 23.46; 24.63; 25.22; 25.49; 25.91; 26.72; 28.45; 29.38; 31.39; 31.82; 32.76; 33.61; 33.74; 34.27; 34.91; 35.53; 39.36; and 39.73.

In certain embodiments, form I of the crystalline HCl salt of a compound of formula (I) has an XRD pattern substantially as shown in FIG. 1.

In certain embodiments, form II of the crystalline HCl has 2θ 8.34; 18.83; and 21.10. In further embodiments, form II has 2θ values 6.26; 8.34; 15.82; 18.83; 21.10; 23.42; 24.10; 24.45; 25.25; and 25.74. In yet further embodiments, form II has 2θ values 6.26; 8.34; 11.02; 12.58; 14.80; 15.61; 15.82; 17.58; 18.20; 18.83; 19.81; 20.00; 21.10; 22.58; 23.42; 24.10; 24.45; 25.25; 25.74; 26.36; 27.83; 28.70; 29.84; 30.46; 31.81; and 32.38. In yet further embodiments, form II has 2θ values 3.10; 6.26; 8.34; 9.04; 9.96; 11.02; 12.58; 13.47; 14.80; 15.61; 15.82; 16.15; 17.58; 18.20; 18.83; 19.81; 20.00; 21.10; 22.02; 22.58; 23.42; 24.10; 24.45; 25.25; 25.74; 26.36; 27.22; 27.83; 28.70; 29.84; 30.46; 31.81; 32.38; 33.23; 35.68; 36.57; 37.40; 39.36; and 41.79.

In certain embodiments, form II of the crystalline HCl salt of a compound of formula (I) has an XRD pattern substantially as shown in FIG. 2.

In certain embodiments, the salt of the compound of formula (I) is a di(hydrochloride) salt. In certain such embodiments, the salt is amorphous.

In certain embodiments, the free base of the present invention can assemble into more than one crystal formation. In an exemplary embodiment, the crystalline free base of the compound having the structure of formula (I) exists as either "form A", "form B", or a mixture thereof, as described in detail below.

In certain embodiments, the invention relates to a free base crystalline compound of formula (I). In certain embodiments, Form B of the crystalline free base has 2θ values 18.39; 19.10; 21.37; 24.65. In further embodiments, Form B of the crystalline free base has 2θ values 7.92; 18.39; 19.10; 20.12; 21.37; 24.10; 24.65; 25.14. In still further embodiments, Form B of the crystalline free base has 2θ values 7.32; 7.92; 11.98; 15.54; 15.87; 18.06; 18.39; 19.10; 20.06; 20.12; 21.37; 22.41; 22.74; 24.10; 24.65; 25.14; 25.78; 27.32. In further embodiments, Form B of the crystalline free base has 2θ values 3.64; 7.32; 7.92; 8.53; 9.30; 9.38; 11.02; 11.98; 14.70; 15.54; 15.87; 16.50; 16.59; 18.06; 18.39; 19.10; 20.06; 20.12; 20.61; 21.37; 21.89; 22.41; 22.74; 23.72; 24.10; 24.65; 25.14; 25.78; 26.49; 27.32; 27.55; 28.26; 29.88; 31.20; 31.80; 31.52; 32.80; 34.30; 35.20; 36.41; 38.53; 40.08; 40.94; and 43.86. In other embodiments, Form B of the crystalline free base has an XRD pattern substantially as shown in FIG. 6.

In certain embodiments, Form A of the crystalline free base has 2θ values 7.57; 18.50; 18.69. In certain embodiments, Form A of the crystalline free base has 2θ values 7.57; 9.67; 11.00; 12.93; 15.20; 18.50; 18.69; 23.33; 24.87. In certain embodiments, Form A of the crystalline free case has 2θ values 5.47; 7.57; 9.67; 11.00; 12.93; 14.14; 15.20; 17.74; 18.50; 18.69; 19.40; 20.54; 21.13; 23.33; 24.37; 24.87; 25.52. In further embodiments, Form A of the crystalline free base has 2θ values 5.47; 6.01; 7.57; 9.20; 9.67; 10.15; 11.00; 12.93; 14.14; 15.20; 15.81; 16.56; 17.74; 18.50; 18.69; 19.40; 19.94; 20.54; 20.59; 21.13; 22.00; 22.60; 23.33; 23.98; 24.37; 24.87; 25.52; 26.27; 26.62; 27.79; 29.59; 30.64; 33.30; 35.01; 37.93; 38.72. In other embodiments, Form A of the crystalline free base has an XRD pattern substantially as shown in FIG. 7.

In certain embodiments, a crystalline compound of formula (I) is not solvated (e.g., the crystal lattice does not comprise molecules of a solvent). In certain alternative embodiments, a crystalline compound of formula (I) is solvated.

In certain embodiments, the crystalline salt compounds of the invention may be salts of prodrugs of the compound of formula (I), e.g., wherein a C(O)—NH moiety in the parent compound is derivatized to replace the hydrogen atom of the amide with a group that can be hydrolyzed or otherwise cleaved to restore the C(O)—NH moiety. In certain such embodiments, the prodrug is metabolized to the active parent compound in vivo.

In certain embodiments, the invention relates to a pharmaceutical composition comprising a crystalline compound or a crystalline salt of a compound of formula (I) and one or more pharmaceutically acceptable excipients. In certain embodiments, the pharmaceutical composition is selected from tablets, capsules, and suspensions.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal.

Methods of Making the Crystalline Salts

In certain embodiments, the invention relates to a method for the preparation of a crystalline salt of a compound having the structure of formula (I), comprising a) providing a freebase mixture of a compound of formula (I) in a first organic solvent; b) contacting the freebase mixture with a reagent solution comprising an acid and optionally a second organic solvent under conditions sufficient to form a mixture comprising a salt of the compound of formula (I); and c)

crystallizing the salt of the compound of formula (I) from the mixture comprising a salt of the compound of formula (I).

In certain embodiments, the mixture comprising a salt of the compound of formula (I) formed in step b) is a solution. In certain embodiments, the mixture formed in step b) is a slurry or a suspension.

In certain embodiments, the mixture comprising the salt of the compound of formula (I) is a solution, and the step of crystallizing the salt from the mixture comprises bringing the solution to supersaturation to cause the salt of the compound of formula (I) to precipitate out of solution.

In certain embodiments, bringing the mixture comprising the salt of a compound of formula (I) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the salt of a compound of formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the salt crystals, e.g. by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise the step of drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, the freebase mixture of a compound of formula (I) in a first organic solvent is a slurry. In certain embodiments, the freebase mixtures of a compound of formula (I) in a first organic solvent is a solution.

In certain embodiments, the first organic solvent and the second organic solvent, if present, comprise acetonitrile, N,N-dimethylacetamide (DMA), dimethylformamide (DMF), dimethylsulfoxide (DMSO), ethanol, ethyl acetate, heptanes, hexanes, isopropyl acetate, methanol, methylethyl ketone, N-methyl-2-pyrrolidone (NMP), tetrahydrofuran, toluene, 2-propanol, 1-butanol, water, or any combination thereof. In certain preferred embodiments, the organic solvent is ethanol, toluene, tetrahydrofuran, or acetonitrile. In an example embodiment, the first organic solvent and the second organic solvent each independently comprise ethanol or acetonitrile. In another example embodiment, the first organic solvent and the second organic solvent each independently comprise dimethylsulfoxide or ethanol. In another example embodiment, the first organic solvent and the second organic solvent each independently comprise N-methyl-2-pyrrolidone or ethanol.

In certain embodiments, the first organic solvent and the second organic solvent, if present, are the same. In alternative embodiments, the first organic solvent and the second organic solvent, if present, are different.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is ethanol.

In certain embodiments, washing the crystals comprises washing the crystalline compound of formula (I) with a solvent or a mixture of one or more solvents, which are described above. In certain embodiments, the solvent or mixture of solvents is cooled prior to washing.

In certain embodiments, the acid is hydrochloric acid, p-toluenesulfonic acid, methanesulfonic acid, nitric acid, or hydrobromic acid. In certain embodiments of the method, in a reaction vessel in which the freebase slurry and reagent solution come into contact with one another, the acid of the reagent solution is in a molar ratio that is from about 1.0 to about 1.5 times the molar amount of the compound of formula (I) in the freebase slurry.

Uses of Enzyme Inhibitors

Glutamine plays an important role as a carrier of nitrogen, carbon, and energy. It is used for hepatic urea synthesis, for renal ammoniagenesis, for gluconeogenesis, and as respiratory fuel for many cells. The conversion of glutamine into glutamate is initated by the mitochondrial enzyme, glutaminase ("GLS"). There are two major forms of the enzyme, K-type and L-type, which are distinguished by their Km values for glutamine and response to glutamate, wherein the Km value, or Michaelis constant, is the concentration of substrate required to reach half the maximal velocity. The L-type, also known as "liver-type" or GLS2, has a high Km for glutamine and is glutamate resistant. The K-type, also known as "kidney-type or GLS1, has a low Km for glutamine and is inhibited by glutamate. An alternative splice form of GLS1, referred to as glutmainase C or "GAC", has been identified recently and has similar activity characteristics of GLS1. In certain embodiments, the compounds may selectively inhibit GLS1, GLS2 and GAC. In a preferred embodiment, the compounds selectively inhibit GLS1 and GAC.

In addition to serving as the basic building blocks of protein synthesis, amino acids have been shown to contribute to many processes critical for growing and dividing cells, and this is particularly true for cancer cells. Nearly all definitions of cancer include reference to dysregulated proliferation. Numerous studies on glutamine metabolism in cancer indicate that many tumors are avid glutamine consumers.

In certain embodiments, the invention is a method for treating or preventing cancer or an immunological or neurological disease utilizing a crystalline compound or a crystalline salt of a compound of formula (I) as described herein.

As used herein, a therapeutic that "prevents" a disorder or condition refers to a compound that, in a statistical sample, reduces the occurrence or frequency of the disorder or condition in the treated sample relative to an untreated control sample, or delays the onset or reduces the severity of one or more symptoms of the disorder or condition relative to the untreated control sample. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

In certain embodiments, the cancer may be one or a variant of Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumors, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Extracranial Germ Cell Tumor, Extragonadal Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Metastatic, Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Gestational Trophoblastic Tumor, Unknown Primary, Unusual Cancers of Childhood, Urethral Cancer, Uterine Cancer, Uterine Sarcoma, Waldenström Macroglobulinemia, and Wilms Tumor.

In some instances, oncogenic mutations promote glutamine metabolism. Cells expressing oncogenic K-Ras exhibt increased ultilization of glutamine. In certain embodiments, the cancer cells have a mutated K-Ras gene. In certain embodiments, the cancer is associated with tissue of the bladder, bone marrow, breast, colon, kidney, liver, lung, ovary, pancreas, prostate, skin or thyroid. The c-Myc gene is known to be altered in numerous cancers. Increased Myc protein expression has been correlated with increased expression of glutaminase, leading to up-regulation of glutamine metabolism. In certain embodiments, the cancer cells have an oncogenic c-Myc gene or elevated Myc protein expression. In some embodiments, the cancer is associated with tissue of the bladder, bone, bowel, breast, central nervous system (e.g., brain), colon, gastric system (such as stomach and intestine), liver, lung, ovary, prostate, muscle, and skin.

The most common type of renal cell carcinoma (RCC), clear cell type (ccRCC) is closely associated with von Hippel-Lindau (VHL) gene mutations. VHL-deficient cell lines have been shown to have an increased requirement for glutamine due to a loss of ability to make fatty acids from glucose (Metallo et al, Nature 2013). This dependency on glutamine makes the cells susceptible to glutaminase inhibitors (Gameiro et al., Cell Metab. 2013). Certain embodiments of the invention relate to the use of the compounds described herein for the treatment of VHL-deficient carcinomas. In certain embodiments the cancer is RCC. In certain embodiments the cancer is ccRCC.

Glutaminase inhibition may be effective in certain rare cancers that have mutations or deletions of the TCA cycle enzymes including fumarate hydratase (FH), succinate dehydrogenase (SDH), or isocitrate dehydrogenase (IDH). Glutamate feeds into the TCA cycle upstream of where these mutations or deletions occur. Published studies indicate that glutamine metabolism is important in the synthesis of fumarate and succinate. In addition to FH and SDH, there is evidence that glutamine contributes to the production of 2-hydroxyglutatrate, another driver of tumor formation that accumulates in patients with tumors harboring mutations in the enzyme isocitrate dehydrogenase. Thus, inhibitors of glutaminase may block the effect of these mutations or deletions by limiting the availability of upstream starting materials. Rare mutations in FH lead to the development of hereditary leiomyomatosis and renal cell cancer (HLRCC), where patients can develop tumors of the skin, uterus or kidneys. Some gastrointestinal stromal tumors (GIST), arise from the lack of expression of SDH, and often hereditary. Other SDH-loss-of-function mutations are found in patient harboring a rare head and neck cancer, known as paraganglioma, and a rare adrenal or extra-adrenal cancer, known as pheochromocytoma, and a rare subset clear cell RCC. Some patients with glioma, a form of brain cancer, chondrosarcoma, a rare bone cancer, cholangiocarcinoma, a rare bile duct tumor, AML, high risk myeldysplasia/myeloproliferative disorders, a group of blood disorders, have IDH1 or IDH2 driver mutations. In certain embodiments of the invention, compounds described herein can be used for the treatment of disease identified with a FH, SDH or IDH (1 and 2) mutation. In certain embodiments the disease is hereditary leiomyomatosis or renal cell cancer (HLRCC). In certain embodiments the disease is GIST, paraganglioma, pheochromocytoma, or clear cell RCC. In certain embodiments, the disease is glioma, chondrosarcoma, cholangiocarcinoma, AML, or myelodysplasia/myeloproliferative disorder.

While many cancer cells depend on exogenous glutamine for survival, the degree of glutamine dependence among tumor cell subtypes may make a population of cells more susceptible to the reduction of glutamine. As an example, gene expression analysis of breast cancers has identified five intrinsic subtypes (luminal A, luminal B, basal, HER2+, and normal-like). Although glutamine deprivation has an impact on cell growth and viability, basal-like cells appear to be more sensitive to the reduction of exogenous glutamine. This supports the concept that glutamine is a very important energy source in basal-like breast cancer cell lines, and suggests that inhibition of the glutaminase enzyme would be beneficial in the treatment of breast cancers comprised of basal-like cells. Triple-negative breast cancer (TNBC) is characterized by a lack of estrogen receptor, progesterone receptor and human epidermal growth factor receptor 2 expression. It has a higher rate of relapse following chemotherapy, and a poorer prognosis than with the other breast cancer subtypes. Interestingly, there appears to be significant similarities in metabolic profiling between TNBC cells and basal-like breast cancer cells (unpublished data). Therefore, certain embodiments of the invention relate to the use of the compounds described herein for the treatment of TNBC and basal-type breast cancers.

Cachexia, the massive loss of muscle mass, is often associated with poor performance status and high mortality rate of cancer patients. A theory behind this process is that tumors require more glutamine than is normally supplied by diet, so muscle, a major source of glutamine, starts to break down in order to supply enough nutrient to the tumor. Thus, inhibition of glutaminase may reduce the need to breakdown muscle. In certain embodiments, the invention relates to the use of the present compounds to prevent, inhibit or reduce cachexia.

The most common neurotransmitter is glutamate, derived from the enzymatic conversion of glutamine via glutaminase. High levels of glutamate have been shown to be neurotoxic. Following traumatic insult to neuronal cells, there occurs a rise in neurotransmitter release, particularly glutamate. Accordingly, inhibition of glutaminase has been hypothesized as a means of treatment following an ischemic insult, such as stroke (Newcomb, PCT WO 99/09825). Huntington's disease is a progressive, fatal neurological condition. In genetic mouse models of Huntington's disease, it was observed that the early manifestation of the disease correlated with dysregulated glutamate release. In HIV-associated dementia, HIV infected macrophages exhibit upregulated glutaminase activity and increased glutamate release, leading to neuronal damage. Similarly, in another neurological disease, the activated microglia in Rett Syndrome release glutamate causing neuronal damage. The release of excess glutamate has been associated with the up-regulation of glutaminase. In mice bred to have reduced glutaminase levels, sensitivity to psychotic-stimulating drugs, such as amphetamines, was dramatically reduced, thus suggesting that glutaminase inhibition may be beneficial in the treatment of schizophrenia. Bipolar disorder is a devastating illness that is marked by recurrent episodes of mania and depression. This disease is treated with mood stabilizers such as lithium and valproate; however, chronic use of these drugs appear to increase the abundance of glutamate receptors, which may lead to a decrease in the drug's effectiveness over time. Thus, an alternative treatment may be to reduce the amount of glutamate by inhibiting glutaminase. This may or may not be in conjunction with the mood stabilizers. Memantine, a partial antagonist of N-methyl-D-aspartate receptor (NMDAR), is an approved therapeutic in the treatment of Alzheimer's disease. Currently, research is being conducted looking at memantine as a means of treating vascular dementia and Parkinson's disease. Since memantine has been shown to partially block the NMDA glutamate receptor also, it is not unresasonable to speculate that decreasing glutamate levels by inhibiting glutaminase could also treat Alzheimer's disease, vascular dementia and Parkinson's disease. Alzheimer's disease, bipolar disorder, HIV-associated dementia, Huntington's disease, ischemic insult, Parkinson's disease, schizophrenia, stroke, traumatic insult and vascular dementia are but a few of the neurological diseases that have been correlated to increased levels of glutamate. Thus, inhibiting glutaminase with a compound described herein can reduce or prevent neurological diseases. Therefore, in certain embodiments, the compounds may be used for the treatment or prevention of neurological diseases.

Activation of T lymphocytes induces cell growth, proliferation, and cytokine production, thereby placing energetic and biosynthetic demands on the cell. Glutamine serves as an amine group donor for nucleotide synthesis, and glutamate, the first component in glutamine metabolism, plays a direct role in amino acid and glutathione synthesis, as well as being able to enter the Krebs cycle for energy production. Mitogen-induced T cell proliferation and cytokine production require high levels of glutamine metabolism, thus inhibiting glutaminase may serve as a means of immune modulation. In multiple sclerosis, an inflammatory autoimmune disease, the activated microglia exhibit up-regulated glutaminase and release increased levels of extracellular glutamate. Glutamine levels are lowered by sepsis, injury, burns, surgery and endurance exercise. These situations put the individual at risk of immunosuppression. In fact, in general, glutaminase gene expression and enzyme activity are both increased during T cell activity. Patients given glutamine following bone marrow transplantation resulted in a lower level of infection and reduced graft v. host disease. T cell proliferation and activation is involved in many immunological diseases, such as inflammatory bowel disease, Crohn's disease, sepsis, psoriasis, arthritis (including rheumatoid arthritis), multiple sclerosis, graft v. host disease, infections, lupus and diabetes. In certain embodiments of the invention, the compounds described herein can be used to treat or prevent immunological diseases.

Hepatic encephalopathy (HE) represents a series of transient and reversible neurologic and psychiatric dysfunction in patients with liver disease or portosystemic shunting. HE is not a single clinical entity and may reflect reversible metabolic encephalopathy, brain atrophy, brain edema, or a combination of these factors; however, the current hypothesis is that the accumulation of ammonia, mostly derived from the intestine, plays a key role in the pathophysiology. The deamination of glutamine in small intestine, renal and muscle synthesis all contribute to ammonia production. Impaired hepatic clearance caused by hepatocellular clearance or portosystemic shunting causes increased accumulation of ammonia. Ammonia toxicity affects astrocytes in the brain via glutamine synthetase, which metabolizes the ammonia to produce increased glutamine. Glutamine, in turn, attracts water into the astrocytes, leading to swelling and oxidative dysfunction of the mitochondria. The resulting cerebral edema is thought to contribute to neurologic dysfunction seen in HE. In certain embodiments of the invention, the compounds described herein can be used to treat or prevent HE.

Primary sensory neurons in the dorsal root ganglion have been shown to elevate their glutaminase enzyme activity following inflammation. It is believed that the resulting increased glutamate production contributes to both central and peripheral sensitization, identified as pain. An aspect of the invention is the use of the present compounds herein for the treatment or diminishment of pain. In certain embodiments, the pain can be neuropathic pain, chemotherapy-induced pain or inflammatory pain.

High blood glucose levels, high insulin levels, and insulin resistance are risk factors for developing diabetes mellitus. Similarly, high blood pressure is a risk factor for developing cardiovascular disease. In a recent report from a large human cohort study, these four risk factors were inversely correlated with glutamine-to-glutamate ratios in the blood stream. Furthermore, plasma glutamine-to-glutamate ratios were inversely correlated with the eventual incidence of diabetes mellitus over 12 years. Experiments with animal models were consistent with these findings. Mice fed glutamine-rich diets exhibited lower blood glucose levels in a glucose tolerance test after 6 hours of fasting, and intraperitoneal injection of glutamine into mice rapidly decreased their blood pressure. Therefore, it is plausible that glutaminase inhibitors, which cause increased glutamine levels and decrease glutamate levels, would decrease the incidence of diabetes mellitus and cardiovascular disease. In particular, the liver and small intestine are major sites of glutamine utilization in diabetic animals, and glutaminase activity is higher than normal in these organs in streptozotocin-induced diabetic rats (Watford et al, Biochem J, 1984; Mithieux et al, Am J Physiol Endrocrinol Metab, 2004). In certain embodiments of the invention, the compounds described herein can be used to treat diabetes. In other embodiments of the invention, the present compounds can be used to reduce high blood pressure.

In certain embodiments, the method of treating or preventing cancer or an immunological or neurological disease may comprise administering a crystalline compound or salt of a compound of formula (I) as described herein conjointly with a chemotherapeutic agent. Chemotherapeutic agents that may be conjointly administered with compounds of the invention include: aminoglutethimide, amsacrine, anastrozole, asparaginase, *Bacillus* Calmette-Guérin vaccine (bcg), bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, or vinorelbine.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuro-blastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDPNP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |

TABLE 1-continued

Exemplary combinatorial therapies for the treatment of cancer.

| Name | Therapeutic agents |
|---|---|
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP | (multiple Melphalan, Prednisone myeloma) |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |

TABLE 1-continued

Exemplary combinatorial therapies for the treatment of cancer.

| Name | Therapeutic agents |
| --- | --- |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the compounds of the invention may be conjointly administered with an immunomodulatory agent. Examples of immunomodulatory agents with which the compounds of the invention may be administered in a combination therapy include granulocyte colony-stimulating factor (G-CSF), interferons, imiquimod, IL-2, IL-7, IL-12, various chemokines, synthetic cytosine phosphate-guanosine (CpG) oligodeoxynucleotides, glucans, and synthetic small molecules such as apremilast, CC-122, CC-11006, CC-10015, lenalidomide, pomalidomide, and thalidomide. In certain embodiments, the immunomodulatory agent is a thalidomide analog, such as those disclosed in WO 1999/46258, WO 2008/033567, WO 2010/093434, WO 2010/093605, WO 2011/100380, and WO 2012/097116.

In certain embodiments, the compounds of the invention may be conjointly administered with an anticancer agent selected from an enzyme inhibitor (such as a kinase inhibitor), a mitotic inhibitor, a DNA-modifying agent, and a cytidine analog. Examples of anticancer agents with which the compounds of the invention may be administered in a combination therapy include microtubule assembly inhibitors, AKT inhibitors, mTOR inhibitors, MEK inhibitors, RTK inhibitors, ATM inhibitors, ATR inhibitors, PI3K inhibitors, EGFR inhibitors, B-Raf inhibitors, C-kit inhibitors, DNA cross-linking agents, DNA intercalating agents, and cytidine analogs. In certain embodiments, the anticancer agent vincristine, carboplatin, cisplatin, gemcitabine, MK2206, everolimus, trametinib, sunitinib, sorafenib, BEZ235, paclitaxel, docetaxel, erlotinib, selumetinib, sirolimus, trametinib, temsirolimus, pazopanib, or GSK1120212.

The proliferation of cancer cells requires lipid synthesis. Normally, acetyl-coA used for lipid synthesis is formed from a mitochondrial pool of pyruvate that is derived from glycolysis. Yet under hypoxic conditions, such as those normally found in a tumor environment, the conversion of pyruvate to acetyl-coA within the mitochondria is down-regulated. Recent studies revealed that under such hypoxic conditions, cells instead largely switch to using a pathway involving the reductive carboxylation of alpha-ketoglutarate to make acetyl-coA for lipid synthesis. The first step in this pathway involves converting glutamine to glutamate via glutaminase enzymes. Subsequently, glutamate is converting to alpha-ketoglutarate, and the resulting alpha-ketoglutarate is converted to isocitrate in a reductive carboxylation step mediated by the isocitrate dehydrogenase enzymes. A switch to this reductive carboxylation pathway also occurs in some renal carcinoma cell lines that contain either impaired mitochondria or an impaired signal for induction of the enzyme responsible for converting glycolytic pyruvate to acetyl-coA. A similar switch occurs in cells exposed to mitochondrial respiratory chain inhibitors such as metformin, rotenone, and antimycin. Therefore, in some embodiments of this invention, we propose using combinations of mitochondrial respiratory chain inhibitors and glutaminase inhibitors to simultaneously increase cancer cells' dependence on glutaminase-dependent pathways for lipid synthesis while inhibiting those very pathways.

The increased dependence on glycolysis in tumor cells is likely because the hypoxic tumor environment impairs mitochondrial respiration. Furthermore, depletion of glucose induces apoptosis in cells transformed with the MYC oncogene. These findings suggest that inhibiting glycolysis would have a therapeutic value in preventing cancer cell proliferation. There are currently many documented glycolytic inhibitors. However, as pointed out by Zhao et al. (2012), "available glycolytic inhibitors are generally not very potent, and high doses are required, which may cause high levels of systemic toxicity." Since cancer cells typically use both glucose and glutamine at higher levels than normal cells, impairing utilization of each of those metabolites will likely have a synergistic effect. Therefore, in some embodiments of this invention, we propose using combinations of glycolytic pathway inhibitors and glutaminase inhibitors. Such glycolytic inhibitors include 2-deoxyglucose, lonidamine, 3-bromopyruvate, imatinib, oxythiamine, rapamycin, and their pharmacological equivalents. Glycolysis can be inhibited indirectly by depleting NAD+ via DNA damage induced by DNA alkylating agents through a pathway activated by poly(ADP-ribose) polymerase. Therefore, in certain embodiments of this invention, we propose using a combination of DNA alkylating agents and glutaminase inhibitors. Cancer cells use the pentose phosphate pathway along with the glycolytic pathway to create metabolic intermediates derived from glucose. Therefore, in another embodiment of this invention, we propose using a combination of pentose phosphate inhibitors such as 6-aminonicotinamide along with glutaminase inhibitors.

In certain embodiments, a crystalline compound or salt of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

In certain embodiments, different compounds of the invention may be conjointly administered with one or more other compounds of the invention. Moreover, such combinations may be conjointly administered with other therapeutic agents, such as other agents suitable for the treatment of cancer, immunological or neurological diseases, such as the agents identified above.

In certain embodiments, the present invention provides a kit comprising: a) one or more single dosage forms of a crystalline compound or salt of the invention; b) one or more single dosage forms of a chemotherapeutic agent as mentioned above; and c) instructions for the administration of the crystalline compound or salt of the invention and the chemotherapeutic agent.

The present invention provides a kit comprising:
a) a pharmaceutical formulation (e.g., one or more single dosage forms) comprising a crystalline compound or salt of the invention; and
b) instructions for the administration of the pharmaceutical formulation, e.g., for treating or preventing any of the conditions discussed above.

In certain embodiments, the kit further comprises instructions for the administration of the pharmaceutical formulation comprising a crystalline compound or salt of the invention conjointly with a chemotherapeutic agent as mentioned above. In certain embodiments, the kit further comprises a second pharmaceutical formulation (e.g., as one or more single dosage forms) comprising a chemotherapeutic agent as mentioned above.

Pharmaceutical Compositions

In certain embodiments, the present invention relates to pharmaceutical compositions comprising a crystalline compound or salt of a compound of formula (I) and one or more pharmaceutically acceptable excipients.

Exemplary pharmaceutically acceptable excipient are presented herein, and include, for example binders, disintegrating agents, lubricants, corrigents, solubilizing agents, suspension aids, emulsifying agents, coating agents, cyclodextrins, and/or buffers. Although the dosage will vary depending on the symptoms, age and body weight of the patient, the nature and severity of the disorder to be treated or prevented, the route of administration and the form of the drug, in general, a daily dosage of from 0.01 to 3000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs.

The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts", J. Pharm. Sci. 66: 1-19).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microcmulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and arc not intended to limit the invention.

EXAMPLES

Materials and Methods
X-Ray Diffraction

Most X-Ray powder diffraction patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

One XRPD pattern was collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640d) was analyzed to verify the observed position of the Si 111 peak is consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

Differential Scanning Calorimetry

DSC was performed using a TA Instruments Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The pans used were Tzero crimped pans, abbreviated "$T_0C$" in the comments field on the thermogram. The sample was heated from −30° C. to 250° C., at 10° C./min (abbreviated "(−30)-250-10 in the Method field on the thermogram).

Thermogravimetric Analysis

TG analysis was performed using a TA Instruments 2050 thermogravimetric analyzer. Temperature calibration was performed using nickel and Alumel™. The sample was placed in a platinum pan and inserted into the TG furnace. The furnace was heated under a nitrogen purge. The sample was heated from 25° C. to 300° C., at 10° C./min (abbreviated "00-300-10" in the method field on the thermogram).

Example 1: Synthetic Protocols for Compound CB-839

Note: Compound 670 is Alternatively Referred to as CB-839

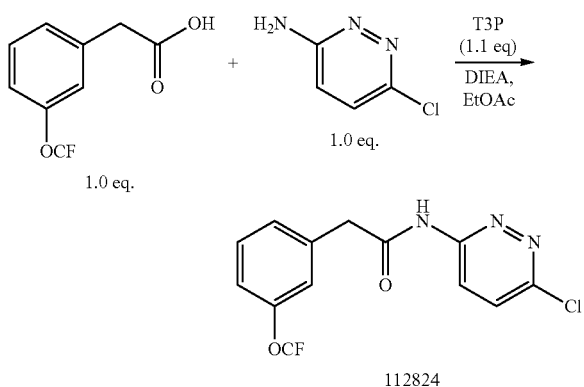

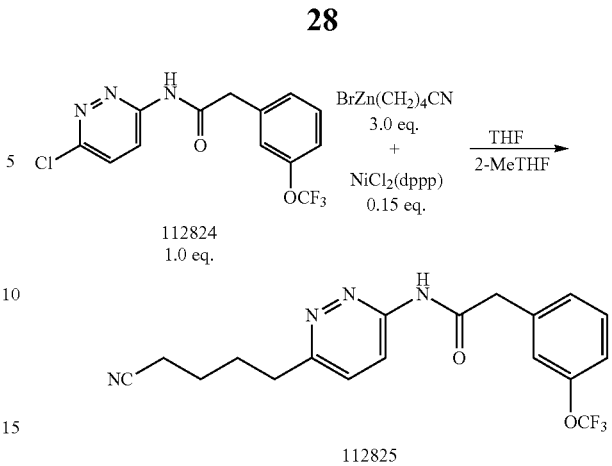

A three liter reaction vessel was charged with 2-(3-(trifluoromethoxy)phenyl)acetic acid (93.34 g, 0.43 mol, 1.0 equiv), 6-chloropyridazin-3-amine (55.51 g, 0.43 mol, 1.0 equiv.), ethyl acetate (1.42 L, 15 vol. versus acid), N,N-diisopropylethylamine (60.92 g, 0.47 mol, 1.1 equiv.) then fitted with a stir bar and temperature probe. The contents of the reaction vessel was placed under an atmosphere of argon (g) and stirred for 15 minutes at which time the mixture was turbid with solids on the bottom of the reaction vessel. To the stirred mixture was added propylphosphonic anhydride (T3P; 300 mL of 50% solution in ethyl acetate, 0.47 mmol, 1.1 equiv.) via a pressure equalizing addition funnel over the course of 40 minutes with a temperature increase of 20.3° C. to 28.1° C. During the course of the addition the color of the mixture became red/orange and the turbidity cleared. The reaction was monitored by TLC (6:4 hexane/ethyl acetate) with a typical run time of 4-6 hours. When the reaction was deemed complete, water (1.5 L) was added and the mixture stirred for an additional 15 minutes. The mixture was transferred to a separatory funnel and the layers separated. The organic layer was washed with water (1.5 L) the layers separated and the organic layer washed with 10% sodium chloride solution (500 mL). The layers were separated, the organic layer transferred to a round bottom flask and the volatiles removed under reduced pressure to give an off-white, yellow solid. To the flask was added hexanes (500 mL) and the contents stirred vigorously for 15 minutes then filtered. The solids were washed again with hexanes (500 mL) and air dried to a constant weight to afford N-(6-chloropyridazin-3-yl)-2-(3-(trifluoromethoxy)phenyl)acetamide (112824): yield of 121.1 g, (85%). $^1$H NMR (300 MHz, DMSO-$d_6$) δ 11.63 (s, 1H), 8.38 (d, J=9.4 Hz, 1H), 7.88 (d, J=9.4 Hz, 1H), 7.52-7.27 (m, 4H), 3.90 (s, 2H).

A five liter reaction vessel was charged with 4-cyanobutylzinc bromide (2 L, 0.5 M in THF, 1000 mmol, 3.0 equiv relative to 112824) followed by dichloro(1,3-bis(diphenylphosphino)propane)nickel (27.10 g, 0.05 mol, 0.15 equiv.), 2-methyltetrahydrofuran (400 mL, 3.6 vol. versus 112824) then fitted with a stir bar and temperature probe. The contents of the reaction vessel were placed under an atmosphere of argon and a 2-methyltetrahydrofuran solution of 112824 (110.56 g, 0.33 mol, 1.0 equiv., 900 mL) was added via a pressure equalizing addition funnel over the course of 45 minutes with a temperature increase of 24.8° C. to 32.9° C. (A 25 minute break was inserted at T=15 minutes, 400 mL added to allow the mixture to cool from 32.6° C. to 28.8° C.) The reaction was monitored by TLC (1:1 hexane/ethyl acetate) with a typical run time of 4-6 hours. When the reaction was deemed complete 0.5 M HCl (1.5 L) was added and stirred for 1 hour at which time a phase break was visible with the lower phase becoming clear and blue. The mixture was transferred to a separatory funnel and the layers separated. The organic layer was washed 2× with an aqueous, saturated ethylenediaminetetraacetic acid solution (1 L), 1× water (1 L), 1×10% sodium chloride solution (500 mL) and the organic layer separated, transferred to a 3 L round bottom flask and the volatiles removed under reduced pressure giving a heavy, deep red oil. The oil was diluted with ethyl acetate (300 mL) and the volatiles removed under reduced pressure (repeat two addition times). The oil was then mixed with hexanes (300 mL) and the volatiles removed under reduced pressure giving rise to an ocher colored, waxy solid. The solid was then stirred with hexanes (500 mL) filtered and air dried to a constant weight to afford N-(6-(4-cyanobutyl)pyridazin-3-yl)-2-(3-(trifluoromethoxy)phenyl)acetamide (112825): yield of 105.7 g, (84%). $^1$H NMR (300 MHz, DMSO-$d_6$) δ 11.41 (s, 1H), 8.28 (d, J=9.2 Hz, 1H), 7.65 (d, J=9.2 Hz, 1H), 7.52-7.27 (m, 4H), 3.89 (s, 2H), 2.92 (t, J=7.5 Hz, 2H), 2.56 (t, J=7.0 Hz, 2H), 1.80 (m, 2H), 1.61 (m, 2H).

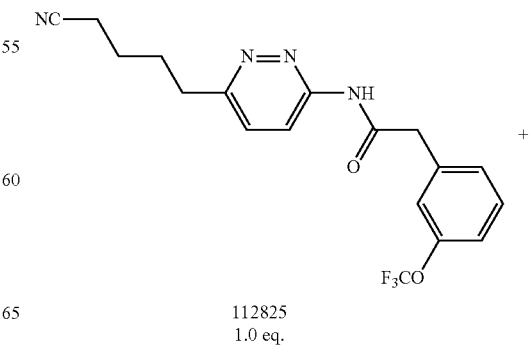

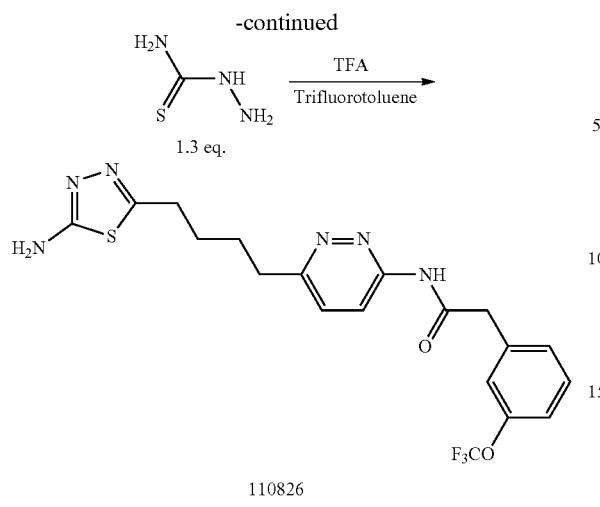

110826

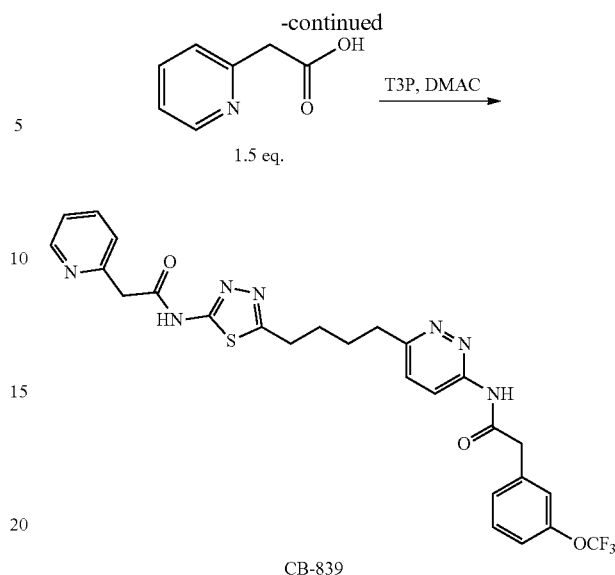

CB-839

112825 (92.3 g, 0.24 mol, 1.0 equiv) was dissolved in trifluorotoluene (923 mL, 10.0 vol versus 112825) in a 3000 mL three neck round bottom flask. Thiosemicarbazide (26.7 g, 0.29 mol, 1.2 equiv.) was charged into the reaction solution. Trifluoroacetic acid (369 mL, 4 vol.) was slowly added to reaction vessel while stirring. The reaction slurry was heated in a 65° C. bath with an open top reflux condenser. The reaction usually goes to completion after 5 hours (determined by LC/MS). The reaction solution was transferred to a 4000 mL erlenmeyer flask and cooled in a 0° C. bath. The pH was adjusted to pH-8 with 2.5N sodium hydroxide(aq) (1800 mL, =20 vol.). Precipitation occurred as the pH became neutral. The slurry was allowed to stir for 30 minutes before rechecking pH. The pH was readjusted if necessary with more 2.5N sodium hydroxide (aq) or 1M HCl to be in the range of pH=6.5-8.5. The precipitate was filtered through a Buchner funnel and rinsed twice with ethyl acetate (2×185 mL, 2 vol). The filtered material was dried under high vacuum to a constant weight to afford N-(6-(4-(5-amino-1,3,4-thiadiazol-2-yl)butyl)pyridazin-3-yl)-2-(3-(trifluoromethoxy)phenyl)acetamide (110826); yield of 94.2 g, (87%). $^1$H NMR (300 MHz, DMSO-$d_6$) δ 11.33 (s, 1H), 8.21 (d, J=9.2 Hz, 1H), 7.58 (d, J=9.2 Hz, 1H), 7.51-7.26 (m, 4H), 6.99 (s, 2H), 3.88 (s, 2H), 2.87 (m, 4H), 1.71 (m, 4H).

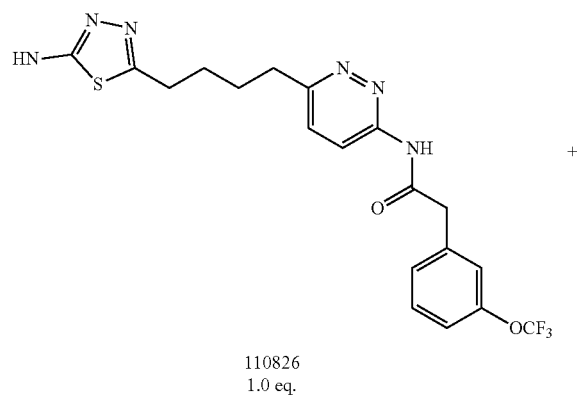

110826
1.0 eq.

To a solution of 110826 (5.5 g, 12.3 mmol, 1.0 equiv.) in N,N-dimethylacetamide (44 mL, 8.0 vol. versus 110826) in a 250 mL three neck round-bottom flask was added 2-pyridylacetic acid (2.56 g, 14.8 mmol, 1.2 equiv.). Propylphosphonic anhydride (11.0 g of 50% solution in ethyl acetate, 17.3 mmol, 1.41 equiv.) was charged into a 25 mL addition funnel and added dropwise to reaction solution at a rate of 5 mL/min. During the addition the internal temperature increased from 20.1° C. to 26.1° C. The reaction usually goes to completion after 4 hours (determined by LC/MS). Reaction solution was then cooled a 0° C. bath and diluted with methyl ethyl ketone (50 mL). To the stirred reaction solution is added H$_2$O (50 mL). The pH was adjusted to pH-6 with 2.5N sodium hydroxide(aq) (28 mL). The yellow precipitate was collected by suction filtration and rinsed with isopropyl alcohol and water (1:1, 50 mL). The air dried solid was then transferred to a 100 mL round bottom flask and slurried in isopropyl alcohol and water (9:1, 50 mL). The slurry was heated to an internal temperature of 65.1° C. for 8 hours and cooled to ambient temperature over 16 hours. The off-white precipitate was collected by suction filtration and rinsed 1× isopropyl alcohol (10 mL). The retentate was dried under high vacuum to a constant weight to afford 2-(pyridin-2-yl)-N-(5-(4-(6-(2-(3-(trifluoromethoxy)phenyl)acetamido)pyridazin-3-yl)butyl)-1,3,4-thiadiazol-2-yl) acetamide (CB-839); yield of 5.27 g (76%). $^1$H NMR (300 MHz, DMSO-$d_6$) δ 12.67 (s, 1H), 11.32 (s, 1H), 8.53-8.49 (m, 1H), 8.22-8.19 (d, J=9.12 Hz, 1H), 7.78-7.76 (t, 1H), 7.58-7.26 (m, 7H), 4.01 (s, 2H), 3.87 (s, 2H), 3.01 (bs, 2H), 2.90 (bs, 2H), 1.73 (bs, 4H).

The XRD pattern of CB-839 crystalline freebase, Form B is shown in FIG. 6. CB-839 freebase, Form B has 2θ values 3.64; 7.32; 7.92; 8.53; 9.30; 9.38; 11.02; 11.98; 14.70; 15.54; 15.87; 16.50; 16.59; 18.06; 18.39; 19.10; 20.06; 20.12; 20.61; 21.37; 21.89; 22.41; 22.74; 23.72; 24.10; 24.65; 25.14; 25.78; 26.49; 27.32; 27.55; 28.26; 29.88; 31.20; 31.80; 31.52; 32.80; 34.30; 35.20; 36.41; 38.53; 40.08; 40.94; and 43.86.

CB-839 crystalline freebase, Form A was prepared as follows:

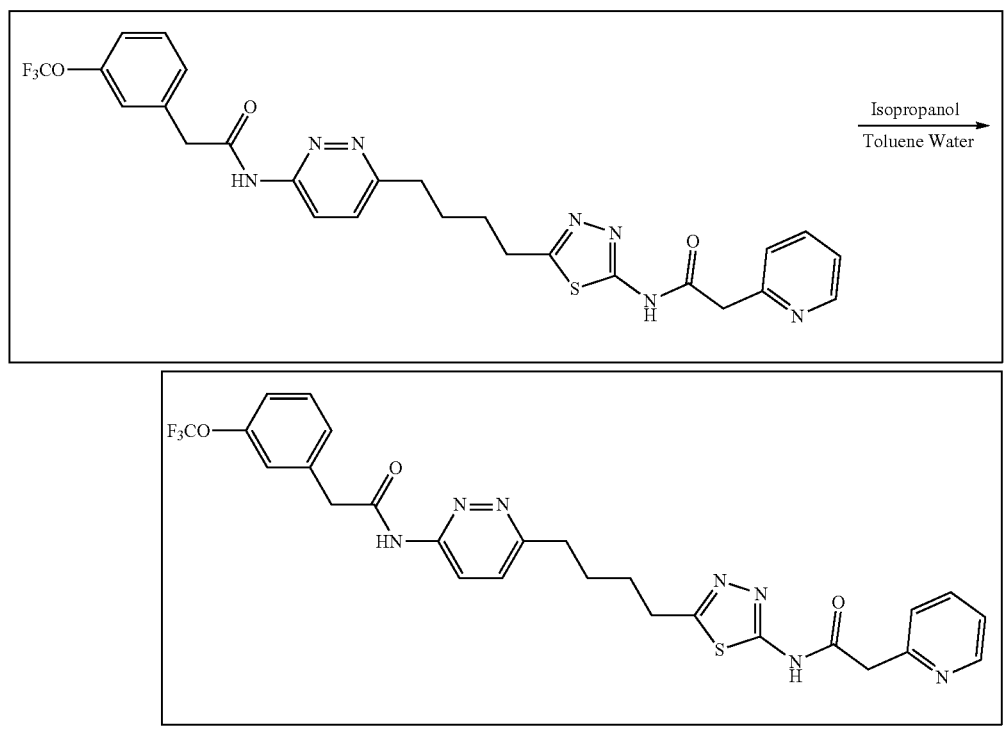

CB-839 free base, Form B (2.02 g, 3.53 mmol) was suspended in a mixture of Isopropanol:Toluene:Water (36.8 mL: 24.6 mL: 3.2 mL, 32 volumes) in a 150 mL 3 neck round bottom flask equipped with magnetic stir bar, hemispherical heating mantle and internal temperature probe. The pale yellow slurry was heated to an internal temperature of 70° C. over 90 minutes. The heating mantle was removed to allow the yellow solution to cool to ambient temperature. The reaction slurry was stirred for 18 hours and then was collected by suction filtration. The filter cake was dried under vacuum in a 70° C. oven to a constant weight to afford crystalline 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide (CB-839), free base, Form A; yield of 1.60 g (79%). $^1$H NMR (300 MHz, DMSO-$d_6$) δ 12.65 (s, 1H), 11.29 (s, 1H), 8.50-8.48 (m, 1H), 8.20-8.17 (d, J=9.11 Hz, 1H), 7.77-7.75 (t, 1H), 7.57-7.54 (m, 1H), 7.47-7.40 (m, 1H), 7.40-7.35 (m, 3H), 7.26-7.24 (m, 2H), 4.00 (s, 2H), 3.85 (s, 2H), 3.01 (bs, 2H), 2.89 (bs, 2H), 1.73 (bs, 4H).

The XRD pattern of CB-839 crystalline freebase, Form A is shown in FIG. 7. CB-839 freebase, Form A has 2θ values 5.47; 6.01; 7.57; 9.20; 9.67; 10.15; 11.00; 12.93; 14.14; 15.20; 15.81; 16.56; 17.74; 18.50; 18.69; 19.40; 19.94; 20.54; 20.59; 21.13; 22.00; 22.60; 23.33; 23.98; 24.37; 24.87; 25.52; 26.27; 26.62; 27.79; 29.59; 30.64; 33.30; 35.01; 37.93; and 38.72.

The DSC data demonstrated that the crystalline, anhydrous CB-839, Form A melts at about 189° C.

Example 2: Preparation of Salts of Compound CB-839

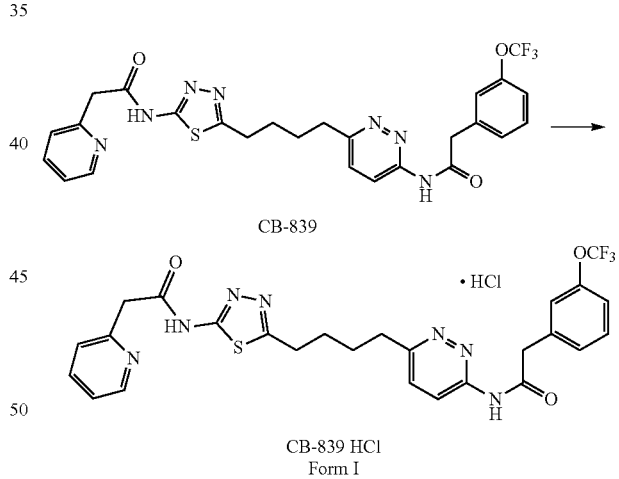

2-(pyridin-2-yl)-N-(5-(4-(6-(2-(3-(trifluoromethoxy) phenyl)acetamido)pyridazin-3-yl)butyl)-1,3,4-thiadiazol-2-yl)acetamide hydrochloride, Form I (CB-839 HCl, Form I)

Compound 670, or CB-839 freebase (4.57 g, 8.00 mmol) was slurried in absolute ethanol (69 mL) in a 250 mL 3-neck round bottom flask equipped with internal temperature probe, 50 mL addition funnel and magnetic stirring. The hemispherical fabric mantle was set to heat the slurry to an internal temperature of 70° C. and held for 90 minutes at this desired temperature. In a closed 50 mL round bottom flask absolute ethanol (23 mL) was stirred with acetyl chloride (0.682 mL, 9.59 mmol) for 5 minutes and then charged into the addition funnel. The ethanolic HCl was added at a rate of 15 mL/min. The internal temperature of the reaction dropped to 60.3° C. during this addition. The slurry went into solution and was clear for 5 minutes at which time precipitate was visible. The resulting slurry was cooled with a wet ice bath to 15° C. in 5 minutes. The bath was removed and the slurry stirred at ambient temperature for 4 hours. The off-white solid was collected by suction filtration and the retentate dried overnight in a 75° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrochloride Form I (CB-839 HCl, 3.98 g). $^1$H NMR (300 MHz, DMSO-$d_6$) δ 12.80 (s, 1H), 11.37 (s, 1H), 8.73 (d, J=5.31 Hz, 1H), 8.23 (m, 2H), 7.75 (d, J=7.93 Hz, 1H), 7.68 (t, J=6.32 Hz, 1H), 7.62 (d, J=9.19 Hz, 1H), 7.47 (t, J=8.09 Hz, 1H), 7.36 (m, 2H), 7.24 (d, J=7.90 Hz, 1H), 4.25 (s, 2H), 3.86 (s, 2H), 3.03 (s, 2H), 2.89 (s, 2H), 1.73 (s, 4H).

The XRD pattern in shown in FIG. 1. CB-839 HCl, Form I has 2θ values 8.62; 9.53; 11.63; 15.89; 16.70; 17.26; 18.18; 19.10; 19.80; 21.09; 22.16; 22.69; 23.46; 24.63; 25.22; 25.49; 25.91; 26.72; 28.45; 29.38; 31.39; 31.82; 32.76; 33.61; 33.74; 34.27; 34.91; 35.53; 39.36; and 39.73.

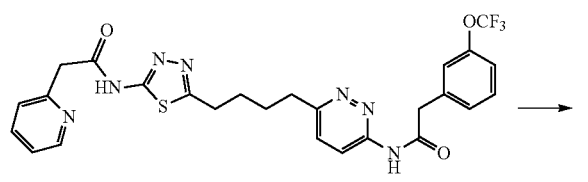

CB-839

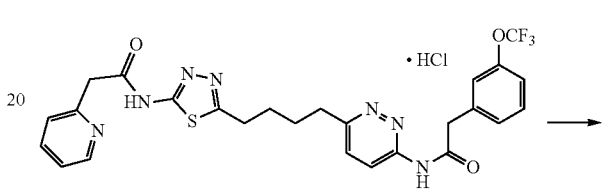

CB-839 HCl
Form II 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrochloride Form II (CB-839 HCl, Form II)

Compound 670, or CB-839 freebase (129.5 g, 227 mmol) was slurried in absolute ethanol (2590 mL) in a 5000 mL 3-neck round bottom flask equipped with internal temperature probe, 1000 mL addition funnel and mechanical stirring. The hemispherical fabric mantle was set to heat the slurry to an internal temperature of 60° C. and held for 60 minutes at this desired temperature. In a closed 1000 mL round bottom flask absolute ethanol (648 mL) was stirred with acetyl chloride (23.1 g, 295 mmol) for 10 minutes and then charged into the addition funnel. The ethanolic HCl was added at a rate of 34 mL/min. The addition funnel was rinsed with absolute ethanol (130 mL). The resulting slurry was allowed to cool to 19° C. over 15 hours. The off-white solid was collected by suction filtration and the retentate dried overnight in a 75° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrochloride Form 11 (CB-839 HCl, 117.2 g). $^1$H NMR (300 MHz, DMSO-$d_6$) δ 12.76 (s, 1H), 11.32 (s, 1H), 8.67 (d, J=4.56 Hz, 1H), 8.21 (d, J=9.16 Hz, 1H), 8.12 (t, J=7.33 Hz, 1H), 7.67 (d, J=7.78 Hz, 1H), 7.59 (d, J=9.19 Hz, 2H), 7.44 (t, J=7.84 Hz, 1H), 7.35 (m, 2H), 7.24 (d, J=7.90 Hz, 1H), 4.18 (s, 2H), 3.85 (s, 2H), 3.00 (s, 2H), 2.89 (s, 2H), 1.73 (s, 4H).

The XRD pattern in shown in FIG. 2. CB-839 HCl, Form II has 2θ values 3.10; 6.26; 8.34; 9.04; 9.96; 11.02; 12.58; 13.47; 14.80; 15.61; 15.82; 16.15; 17.58; 18.20; 18.83; 19.81; 20.00; 21.10; 22.02; 22.58; 23.42; 24.10; 24.45; 25.25; 25.74; 26.36; 27.22; 27.83; 28.70; 29.84; 30.46; 31.81; 32.38; 33.23; 35.68; 36.57; 37.40; 39.36; and 41.79.

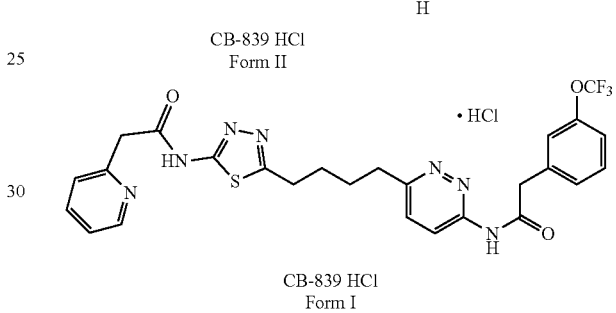

CB-839 HCl
Form II

CB-839 HCl
Form I 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrochloride Form I (CB-839 HCl, Form I)

CB-839 HCl Form II (2.35 g, 3.89 mmol) was slurried in absolute ethanol (71 mL) in a 250 mL 3-neck round bottom flask equipped with internal temperature probe and magnetic stirring. The hemispherical fabric mantle was set to heat the slurry to an internal temperature of 65° C. and held for 60 minutes at this desired temperature. The slurry was seeded with 2% CB-839 HCl Form I crystals (47 mg) and held at temperature for 7.5 hours. The slurry was then cooled to ambient temperature over 18 hours and the off-white solid collected by suction filtration and the retentate dried in a 50° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrochloride Form I (CB-839 HCl, 2.13 g).

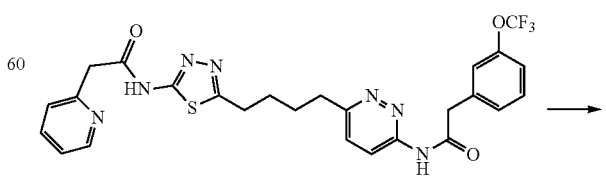

CB-839

-continued

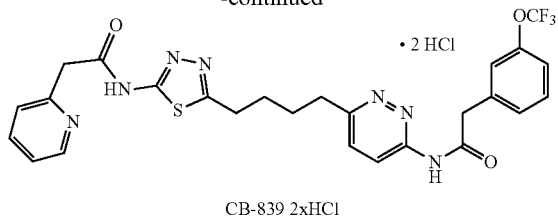

CB-839 2xHCl

2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide dihydrochloride (CB-839 2xHCl)

Compound 670, or CB-839 freebase (1.05 g, 1.84 mmol) was slurried in absolute ethanol (21 mL) in a 100 mL 3-neck round bottom flask equipped with internal temperature probe, 25 mL addition funnel and magnetic stir bar. The hemispherical fabric mantle was set to heat the slurry to an internal temperature of 65° C. and held for 60 minutes at this desired temperature. In a closed 25 mL round bottom flask absolute ethanol (5.3 mL) was stirred with acetyl chloride (640 μL, 9.19 mmol) for 5 minutes and then charged into the addition funnel. The ethanolic HCl was added over 2 minutes and the reaction mixture dissolved into a yellow solution, at which time the heating mantle was removed. Precipitation was observed after 20 minutes at an internal temperature of 38° C. The reaction was further cooled to 19° C. over 18 hours. The slightly yellow solid was collected by suction filtration and the retentate dried overnight in a 60° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide dihydrochloride (CB-839 2xHCl, 754 mg). $^1$H NMR (300 MHz, DMSO-$d_6$) δ 13.05 (s, 1H), 11.55 (s, 1H), 8.87 (d, J=4.74 Hz, 1H), 8.47 (m, 1H), 8.38 (d, J=9.22 Hz, 1H), 7.96 (d, J=7.99 Hz, 1H), 7.90 (t, J=6.72 Hz, 2H), 7.78 (d, J=9.22 Hz, 1H), 7.49 (t, J=8.09 Hz, 1H), 7.39 (m, 2H), 7.28 (d, J=8.50 Hz, 2H), 4.42 (s, 2H), 3.90 (s, 2H), 2.89 (m, 4H), 1.77 (s, 4H).

The CB-839 2xHCl salt is amorphous.

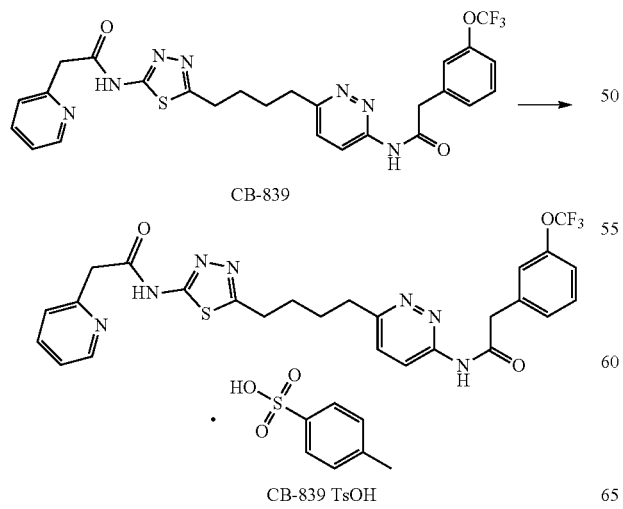

2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide 4-methylbenzenesulfonate (CB-839 TsOH)

Compound 670, or CB-839 freebase (8.20 g, 14.3 mmol) was slurried in absolute ethanol (205 mL) in a 500 mL 3-neck round bottom flask equipped with internal temperature probe, 50 mL addition funnel and magnetic stirring. The hemispherical fabric mantle was set to heat the slurry to an internal temperature of 65° C. and held for 120 minutes at this desired temperature. In a closed 50 mL round bottom flask absolute ethanol (41 mL) was stirred with p-toluenesulfonic acid (3.27 g, 17.2 mmol) for 10 minutes and then charged into the addition funnel. The ethanolic p-toluenesulfonic acid was added at a rate of 14 mL/min. The slurry went briefly into solution and was allowed to cool to 19° C. over 4 hours. The white solid was collected by suction filtration and the retentate dried overnight in a 60° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide 4-methylbenzenesulfonate (CB-839 TsOH, 4.44 g). $^1$H NMR (300 MHz, DMSO-$d_6$) δ 12.77 (s, 1H), 11.32 (s, 1H), 8.70 (t, J=4.65 Hz, 1H), 8.22 (d, J=9.16 Hz, 1H), 8.15 (t, J=7.40 Hz, 1H), 7.65 (d, J=18.70 Hz, 1H), 7.61 (m, 2H), 7.45 (m, 3H), 7.36 (m, 2H), 7.25 (d, J=8.38 Hz, 1H), 7.10 (d, J=7.87 Hz, 2H), 4.18 (s, 2H), 3.85 (s, 2H), 3.02 (s, 2H), 2.89 (s, 2H), 2.28 (s, 3H), 1.74 (s, 4H).

The XRD pattern of CB-839 TsOH is shown in FIG. 3. CB-839 TsOH has 2θ values 5.66; 6.84; 7.97; 11.34; 11.55; 12.04; 13.78; 14.42; 15.44; 15.99; 16.58; 17.09; 18.10; 18.66; 19.69; 20.23; 21.11; 22.03; 22.16; 22.50; 22.84; 23.48; 24.05; 25.59; 25.89; 27.80; 29.35; 30.46; 31.10; 33.82; 35.65; 36.67; 38.93; 39.99; 42.65; and 43.68.

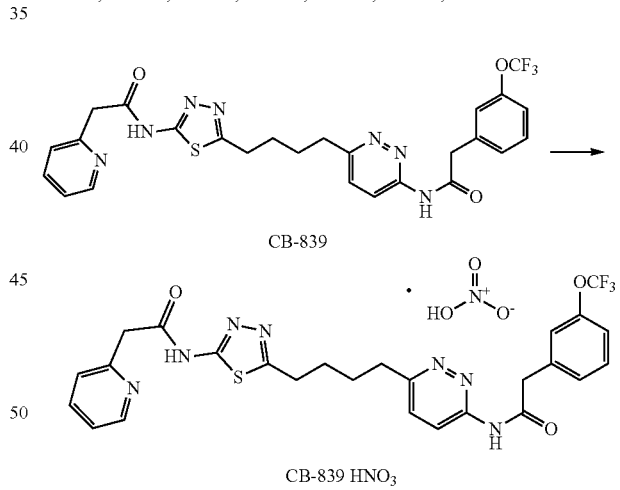

2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide nitrate (CB-839 HNO$_3$)

Compound 570, or CB-839 freebase (498 mg, 0.87 mmol) was slurried in tetrahydrofuran (2 mL) and acetonitrile (3.5 mL) in a 25 mL 3-neck round bottom flask equipped with internal temperature probe and magnetic stir bar. The hemispherical fabric mantle was set to heat the slurry to an internal temperature of 60° C. and held for 60 minutes at this desired temperature. In a vial acetonitrile (200 μL) was stirred with nitric acid (100 μL, 1.13 mmol) for 5 minutes and then added to the slurry. The resulting solution was allowed to cool to 19° C. over 6 hours. The tan solid was collected by suction filtration and the retentate dried overnight in a 60° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide nitrate (CB-839 HNO₃, 150 mg). ¹H NMR (300 MHz, DMSO-d₆) δ 12.85 (s, 1H), 11.36 (s, 1H), 8.76 (d, J=5.16 Hz, 1H), 8.27 (m, 2H), 7.78 (d, J=7.93 Hz, 1H), 7.71 (m, 1H), 7.63 (d, J=9.37 Hz, 1H), 7.49 (t, J=7.917 Hz, 1H), 7.39 (m, 2H), 7.28 (d, J=8.17 Hz, 1H), 4.24 (s, 2H), 3.88 (s, 2H), 3.04 (s, 2H), 2.92 (s, 2H), 1.76 (s, 4H).

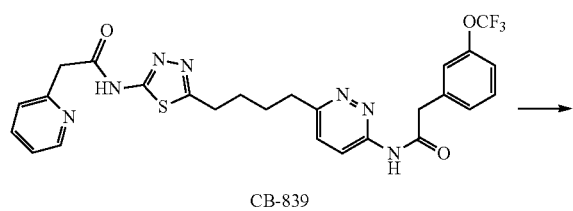

CB-839

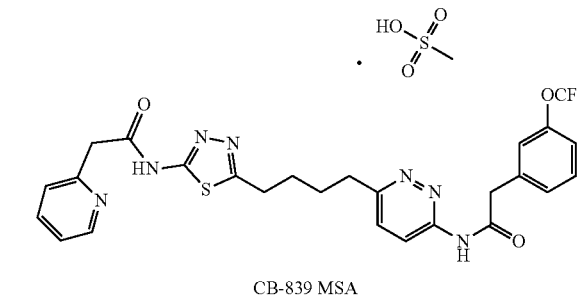

CB-839 MSA 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide methanesulfonate (CB-839 MSA)

Compound 670, or CB-839 freebase (1.55 g, 2.71 mmol) was slurried in absolute Ethanol (23 mL) in a 50 mL 3-neck round bottom flask equipped with internal temperature probe and magnetic stir bar. The hemispherical fabric mantle was set to heat slurry to an internal temperature of 65° C. and was held for 30 minutes at this desired temperature. Methanesulfonic acid (2.71 mmol, 180 µL) was then added to the reaction slurry. The slurry went briefly into solution and was allowed to cool to 19° C. over 5 hours. The off-white solid was collected by suction filtration and the retentate dried overnight in a 60° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide methanesulfonate (CB-839 MSA, 960 mg). ¹H NMR (300 MHz, DMSO-d₆) δ 12.87 (s, 1H), 11.38 (s, 1H), 8.79 (t, J=5.40 Hz, 1H), 8.29 (m, 2H), 7.82 (d, J=7.68 Hz, 1H), 7.76 (m, 1H), 7.64 (d, J=9.10 Hz, 1H), 7.49 (t, J=8.08 Hz, 1H), 7.38 (m, 2H), 7.28 (d, J=8.47 Hz, 1H), 4.27 (s, 2H), 3.88 (s, 2H), 3.05 (s, 2H), 2.92 (s, 2H), 2.35 (s, 3H), 1.76 (s, 4H).

The XRD pattern of CB-839 MSA is shown in FIG. 4. CB-839 MSA has 2θ values 5.86; 7.00; 8.00; 9.37; 10.04; 11.13; 11.76; 13.20; 14.82; 14.42; 15.30; 15.98; 16.50; 17.26; 17.98; 18.88; 19.55; 19.96; 20.25; 21.08; 21.53; 22.07; 22.17; 22.50; 23.09; 23.12; 23.80; 24.05; 24.66; 25.22; 25.73; 26.02; 26.66; 27.13; 27.58; 29.16; 29.53; 30.35; 31.07; 31.87; 32.98; 33.87; 34.34; 36.76; 37.48; 39.35; 40.05; 40.10; and 41.77.

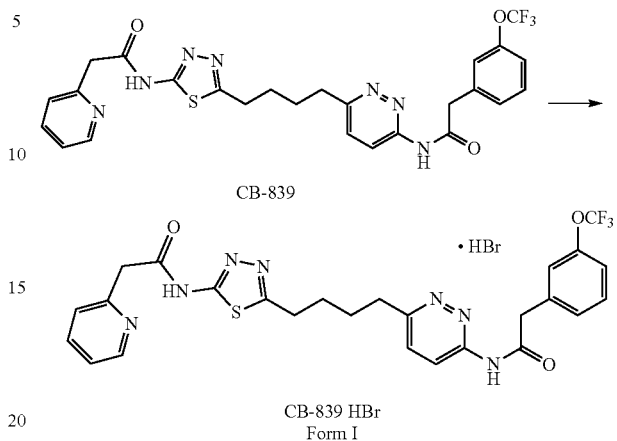

CB-839

CB-839 HBr
Form I 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrobromide (CB-839 HBr)

Compound 670, or CB-839 freebase (1.07 g, 1.87 mmol) was slurried in absolute ethanol (27 mL) in a 50 mL 3-neck round bottom flask equipped with internal temperature probe and magnetic stirring. The hemispherical fabric mantle was set to heat the slurry to an internal temperature of 65° C. and held for 60 minutes at this desired temperature. In a 20 mL scintillation vial absolute ethanol (5 mL) was stirred with acetyl bromide (0.166 mL, 2.25 mmol) for 5 minutes and then charged into the reaction slurry over 2 minutes. The slurry thinned and darkened slightly in color. The slurry was cooled to ambient temperature and stirred for 6.5 hours. The off-white solid was collected by suction filtration and the retentate dried overnight in a 50° C. vacuum oven to afford 2-(pyridin-2-yl)-N-(5-(4-(6-(2-(3-(trifluoromethoxy)phenyl)acetamido)pyridazin-3-yl)butyl)-1,3,4-thiadiazol-2-yl)acetamide hydrobromide Form I (CB-839 HBr, 1.02 g). ¹H NMR (300 MHz, DMSO-d₆) δ 12.80 (s, 1H), 11.33 (s, 1H), 8.73 (d, J=4.47 Hz, 1H), 8.21 (d, J=8.76 Hz, 2H), 7.75 (d, J=7.86 Hz, 1H), 7.68 (m, 1H), 7.60 (d, J=8.89 Hz, 1H), 7.45 (t, J=7.42 Hz, 1H), 7.35 (m, 2H), 7.24 (d, J=7.87 Hz, 1H), 4.21 (s, 2H), 3.84 (s, 2H), 3.00 (s, 2H), 2.88 (s, 2H), 1.72 (s, 4H).

The XRD pattern in shown in FIG. 5. CB-839 HBr has 2θ values 5.08; 6.58; 10.20; 10.83; 12.52; 12.89; 15.19; 15.98; 16.32; 17.28; 18.60; 19.36; 19.96; 20.54; 21.13; 21.76; 22.34; 22.92; 24.44; 25.77; 25.84; 26.43; 26.49; and 30.27.

Example 3: Compound Assays

Compound 670 was assayed in both an in vitro biochemical assay and a cell proliferation assay. Experimental protocols and results of the assays are found in U.S. Pat. No. 8,604,016, or alternatively in U.S. Patent Application Publication No. 2014/0050699 A1.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A crystalline hydrobromide salt of a compound having the structure of formula (I),

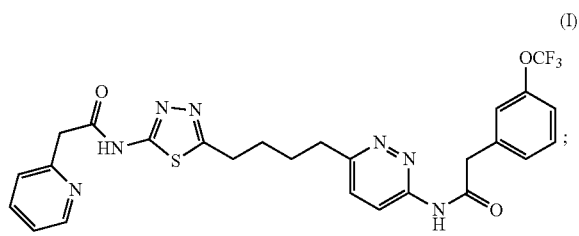 [SMILES: O=C(Cc1cccc(OC(F)(F)F)c1)Nc1ccc(CCCCc2nnc(NC(=O)Cc3ccccn3)s2)nn1]

having 2θ values 5.08; 6.58; 10.83; 20.54; and 21.13.

2. The crystalline salt of claim 1, having 2θ values 5.08; 6.58; 10.20; 10.83; 19.96; 20.54; 21.13; 22.92; 25.84; and 26.49.

3. The crystalline salt of claim 2, having 2θ values 5.08; 6.58; 10.20; 10.83; 12.52; 15.19; 17.28; 19.96; 20.54; 21.13; 21.76; 22.34; 22.92; 25.77; 25.84; 26.43; and 26.49.

4. The crystalline salt of claim 3, having 2θ values 5.08; 6.58; 10.20; 10.83; 12.52; 12.89; 15.19; 15.98; 16.32; 17.28; 18.60; 19.36; 19.96; 20.54; 21.13; 21.76; 22.34; 22.92; 24.44; 25.77; 25.84; 26.43; 26.49; and 30.27.

5. The crystalline salt of claim 4, having an XRD pattern substantially as shown in FIG. 5.

6. A pharmaceutical composition comprising the crystalline salt of claim 1 and one or more pharmaceutically acceptable excipients.

7. A method for preparing a crystalline salt of a compound having the structure of formula (I):

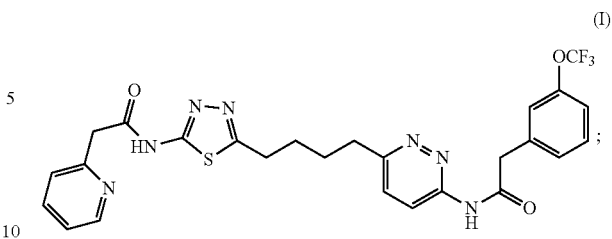

comprising:
a) providing a freebase mixture of a compound of formula (I) in a first organic solvent;
b) contacting the freebase mixture with a reagent solution under conditions sufficient to form a mixture comprising a salt of the compound of formula (I), wherein the reagent solution comprises an acid and optionally a second organic solvent; and
c) crystallizing the salt of the compound of formula (I) from the mixture comprising a salt of the compound of formula (I);
wherein the crystalline salt is a hydrobromide salt.

8. The method of claim 7, wherein the first organic solvent and the second organic solvent, if present, are the same.

9. The method of claim 7, wherein the first organic solvent and the second organic solvent, if present, are different.

10. The method of claim 7, wherein the first organic solvent and the second organic solvent each independently comprise ethanol and/or acetonitrile.

11. The method of claim 7, wherein the acid is hydrobromic acid.

12. The method of claim 7, wherein the acid of step b) exists in the reagent solution in a molar amount that is from about 1.0 to about 1.5 times the molar amount of the compound of formula (I) in the freebase mixture.

13. The method of claim 7, wherein the mixture comprising a salt of the compound of formula (I) is a solution, and the step of crystallizing the salt of the compound of formula (I) from the mixture comprises bringing the solution to supersaturation to cause the salt of the compound of formula (I) to precipitate out of solution.

14. The method of claim 13, wherein the step of bringing the solution to supersaturation comprises slowly adding an anti-solvent, allowing the solution to cool, reducing the volume of the solution, or any combination thereof.

15. The method of claim 7, further comprising isolating the crystalline salt.

16. The method of claim 7, wherein the crystalline salt is the crystalline salt of claim 1.

* * * * *